United States Patent
Schumacher et al.

(10) Patent No.: US 6,699,890 B2
(45) Date of Patent: Mar. 2, 2004

(54) PHOSPHODIESTERASE 4 INHIBITORS

(75) Inventors: Richard A. Schumacher, Monroe, NY (US); William F. Brubaker, Cheshire, CT (US); Michael De Vivo, New York, NY (US); Hans-Jürgen Ernst Hess, Old Lyme, CT (US); Allen Hopper, Glen Rock, NJ (US); Ashok Tehim, Ridgewood, NJ (US); Ruiping Liu, Huntington, NY (US); Axel Unterbeck, Madison, CT (US)

(73) Assignee: Memory Pharmaceuticals Corp., Montvale, NJ (US)

( * ) Notice: Subject to any disclaimer, the term of this patent is extended or adjusted under 35 U.S.C. 154(b) by 0 days.

(21) Appl. No.: 10/051,309

(22) Filed: Jan. 22, 2002

(65) Prior Publication Data

US 2002/0151566 A1 Oct. 17, 2002

Related U.S. Application Data

(60) Provisional application No. 60/262,651, filed on Jan. 22, 2001, provisional application No. 60/267,196, filed on Feb. 8, 2001, and provisional application No. 60/306,140, filed on Jul. 19, 2001.

(51) Int. Cl.$^7$ .................. C07D 213/40; A61K 31/4412; A61K 31/4418
(52) U.S. Cl. .................. 514/352; 514/381; 514/247; 514/315; 514/374; 514/360; 546/194; 546/304; 549/13; 549/200; 549/229
(58) Field of Search ................. 546/194, 304; 549/13, 200, 229; 514/247, 315, 352, 359, 360, 374, 381

(56) References Cited

U.S. PATENT DOCUMENTS

| | | |
|---|---|---|
| 5,591,776 A | 1/1997 | Cavalla et al. |
| 5,622,977 A | 4/1997 | Warrellow et al. |
| 5,633,257 A | 5/1997 | Warrellow et al. |
| 5,679,696 A | 10/1997 | Fenton et al. |
| 5,693,659 A | 12/1997 | Head et al. |
| 5,698,711 A | 12/1997 | Palfreyman |
| 5,710,160 A | 1/1998 | Guay et al. |
| 5,710,170 A | 1/1998 | Guay et al. |
| 5,712,298 A | 1/1998 | Amschler |
| 5,723,460 A | 3/1998 | Warrellow et al. |
| 5,728,712 A | 3/1998 | Montana et al. |
| 5,739,144 A | 4/1998 | Warrellow et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow et al. |
| 5,814,651 A | 9/1998 | Duplantier et al. |
| 5,840,724 A | 11/1998 | Fenton et al. |
| 5,849,770 A | 12/1998 | Head et al. |
| 5,859,034 A | 1/1999 | Warrellow et al. |
| 5,866,593 A | 2/1999 | Warrellow et al. |
| 5,891,896 A | 4/1999 | Warrellow et al. |
| 5,919,937 A | 7/1999 | Lynch et al. |
| 5,935,978 A | 8/1999 | Fenton et al. |
| 5,962,483 A | 10/1999 | Warrellow et al. |
| 5,962,492 A | 10/1999 | Warrellow et al. |
| 6,077,854 A | 6/2000 | Warrellow et al. |
| 6,096,768 A | 8/2000 | Ashton et al. |
| 6,162,830 A | 12/2000 | Connor et al. |
| 6,180,650 B1 | 1/2001 | Frenette et al. |
| 6,200,993 B1 | 3/2001 | Cote et al. |
| 6,204,275 B1 | 3/2001 | Friesen et al. |
| 6,245,774 B1 | 6/2001 | Warrellow et al. |
| 6,255,326 B1 | 7/2001 | Ashton et al. |
| 6,297,264 B1 | 10/2001 | Head et al. |

FOREIGN PATENT DOCUMENTS

| | | |
|---|---|---|
| EP | 0994100 A1 | 4/2000 |
| EP | 1116711 A2 | 7/2001 |
| FR | 2729142 A1 | 7/1996 |
| JP | 11-189577 | 7/1999 |
| WO | WO 93/25517 | 12/1993 |
| WO | WO 94/02465 | 2/1994 |
| WO | WO 94/14742 | 7/1994 |
| WO | WO94/27971 A1 | 12/1994 |
| WO | WO 95/01338 | 1/1995 |
| WO | WO96/21435 A1 | 7/1996 |
| WO | WO 96/23754 | 8/1996 |
| WO | WO96/36620 | * 11/1996 |
| WO | WO 98/58901 | 12/1998 |
| WO | WO99/33806 | * 7/1999 |
| WO | WO 00/64874 | 11/2000 |
| WO | WO00/71129 A1 | 11/2000 |
| WO | WO 01/70738 | 9/2001 |

OTHER PUBLICATIONS

Heilman et al, "Synthesis and Antiinflammatory Evaluation of Substitued Isophthalonitriles, Trimesonitriles, Benzonitriles, and Terephthalonitriles", Journal of Medicinal Chemistry, 1978, vol. 21, No. 9, pp. 906–913, XP–002226236.

Watanabe et al, "Structure–Activity Relationship and Rational Design of 3,4–Dephostatin Derivatives as Protein Tyrosine Phosphatase Inhibitors", Pergamon Tetrahedron, 2000, vol. 56, pp. 741–752.

(List continued on next page.)

Primary Examiner—Rita Desai
(74) Attorney, Agent, or Firm—Millen, White, Zelano, Branigan, P.C.

(57) ABSTRACT

PDE4 inhibition is achieved by novel compounds, e.g., N-substituted aniline and diphenylamine analogs. The compounds of the present invention are of Formula I:

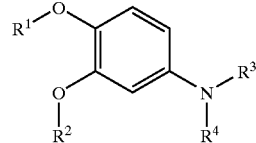

wherein $R^1$, $R^2$, $R^3$ and $R^4$ are as defined herein.

75 Claims, No Drawings

OTHER PUBLICATIONS

Inoue et al, "Steric Tuning in Chiral Ligand Mediated Enantioselective Alkylation of Imines", Tetrahedron: Asymmetry, 1993, vol. 4, No. 7, pp. 1603–1606, XP002226237.

Anil S. Guram et al., "A Simple Catalytic Method for the conversion of Aryl Bromides to Arylamines," Angew. Chem. Int, Ed. Engl., 1995, vol. 34, No. 12, pp. 1348–1350.

Michael S. Driver et al., "A Second–Generation Catalyst for the Aryl Halide Amination: Mixed Secondary Amines from Aryl Halides and Primary Amines Catalyzed by (DPPF)P-dCl$_2$," J. Am. Chem. Soc., 1996, vol. 118, pp. 7217–7218.

Takashi Egawa et al., "Rolipram and its Optical Isomers, Phosphodiesterase 4 Inhibitors, Attenuated the Scopolamine–Induced Impairments of Learning and Memory in Rats," J. Pharmacol., vol. 75, 275–281(1997).

Peng Wang et al., "Expression, Purification, and Characterization of Human cAMP–Specific Phosphodiesterase (PDE4) Subtypes A, B, C, and D,"Biochem. And Biophys. Research Comm., vol. 234, 320–324 (1997).

Domine M. T. Chan et al., "New N– abd O–Arylations with Phenylboronic Acids and Cupric Acetate," Tetrahedron Letters, vol. 39, 2933–2936 (1998).

Mark Barad et al., "Rolipram, a Type IV–Specific Phosphodiesterase Inhibitor Facillitates the Establishment of Long–lasting Long–term Potentiation and Improves Memory," Proc. Natl. Acad. Sci., vol. 95, pp. 15020–15025 (Dec. 1998).

Miles D. Houslay et al., "The Multienzyme PDE4 Cyclic Adenosine Monophosphate–Specific Phosphodiesterase Family: Intracelllular Targeting, Regulation, and Selective Inhibition by Compounds Exerting Anti–inflammatory and Antidepressant Actions," Advances in Pharmacology, vol. 44, pp. 225–342, 1998.

John Hartwig et al., "Room–Temperature Palladium–Catalyzed Amination of Aryl Bromides and Chlorides and Extended Scope of Aromatic C–N Bond Formation with a Commercial Ligand," J. Org. Chem., 1999, vol. 64, pp. 5575–5580.

Han–Ting Zhang et al., "Inhibition of Cyclic AMP Phosphodiesterase (PDE4) Reverses Memory Deficits Associated with NDMA Receptor Antagonism," Neuropsychopharmacology, 2000, vol. 23, pp. 198–204.

Han–Ting Zhang et al., "Effects of Rolipram on Scopolamine–induced Impairment of Working and Reference Memory in the Radial–arm Maze tests in Rats," Psychopharmacology (Berl) Jun. 2000;150(3)pp. 311–316.

T.W. Greene et al., *Protective Groups in Organic Synthesis*, 3$^{rd}$ Edition, Chapter 3, "Protection for Phenols and Catechols," pp. 246–292, John Wiley & Sons, 1999.

Thomas C. McKenzie et al., "The Gomberg–Bachmann Reaction of Purines", J. Heterocyclic Chem., May–Jun., 1987, pp. 859–861, vol. 24.

Vasu Nair et al., "Novel, Stable Congeners of Antiretroviral Compound 2', 3'– Dideoxyadenosine," J. Am. Chem. Soc., 1989, pp. 8502–8504, vol. 111.

Vasu Nair et al., "Synthesis Of Congeners Of Adenosine Resistant To Deamination By Adenosine Deaminase," J. Chem. Soc Comm., 1989, pp. 878–879.

James L. Kelley et al., "Synthesis and Structure–Activity Relationships of 2–Substituted–6–(dimethylamino)–9–(4–methylbenzyl)–9H–purines with Antirhinovirus Activity," J. Med. Chem., 1989, pp. 218–224, vol. 32.

James E. Kelley et al., "Antirhinovirus structure–activity relationships of 6–substituted–9–(4–methylbenzyl)–2–trifluoromethyl–9H–purines," Eur. J. Med. Chem., 1990, pp. 131–135, vol. 25.

Roger J. Schilling et al., "A High–Throughput Assay For Cyclic Nucleotide Phosphodiesterases," Analytical Biochemistry, 1994, pp. 154–158, vol. 215.

Donald V. Daniels et al., "A Semiautomated Method for the Assay of Cyclic Adenosine 5'–Monophosphate Phosphodiesterase," Analytic Biochemistry, 1996, pp. 367–369, vol. 236.

Jean–Jacques Bourguignon et al., "9–Benzyladenines: Potent and Selective cAMP Phosphodiesterase Inhibitors," J. Med. Chem, 1997, pp. 1768–1770, vol. 40.

James L. Kelley et al., "6–(Alkylamino)–9–alkylpurines. A New Class of Potential Antipsychotic Agents," J. Med. Chem., 1997, pp. 3207–3216, vol. 40.

Hiroyuki Sawanishi et al., "Selective Inhibitors of Cyclic AMP–Specific Phosphodiesterase: Heterocycle–Condensed Purines", J. Med. Chem., 1997, pp. 3248–3253, vol. 40.

J.E. Sounnes et al., "Proposal for Pharmacologically Distinct Conformers of PDE4 Cyclic AMP Phosphodiesterases", Cell Signal, 1997, pp. 227–236. vol. 9, No. 3–4.

Mary Elizabeth Bach et al., "Age–related defects in spatial memory are correlated with defects in the late phase of hippocampal long term potentiation in vitro and are attenuated by drugs that enhance the cAMP signaling pathway", Proc. Natl. Acad. Sci. USA, Apr. 1999, pp. 5280–5285, vol. 96.

Elisabeth Boichot et al., "Anti–Inflammatory Activities of a New Series of Selective Phosphodiesterase 4 Inhibitors Derived from 9– Benzyladenine," The Journal Of Pharmacology And Experimental Therapeutics, 2000, pp. 647–653, Vol 292, No. 2.

* cited by examiner

PHOSPHODIESTERASE 4 INHIBITORS

This application claims the benefit of U.S. Provisional application Serial No. 60/262,651, filed Jan. 22, 2001, U.S. provisional application Serial No. 60/267,196, filed Feb. 8, 2001, and U.S. Provisional application Serial No. 60/306,140, filed Jul. 19, 2001.

FIELD OF THE INVENTION

The present invention relates generally to the field of phosphodiesterase 4 (PDE4) enzyme inhibition. More specifically this invention relates to selective PDE4 inhibition by novel compounds, e.g., N-substituted aniline and diphenylamine analogs, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.*, 234, 320–324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

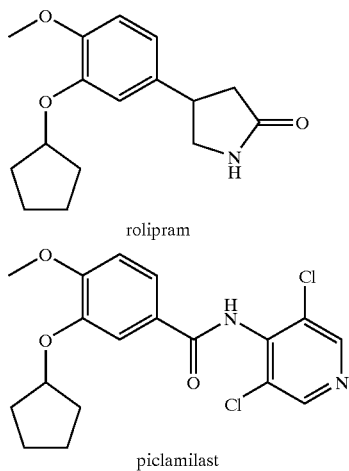

rolipram piclamilast

In addition to such compounds as rolipram, xanthine derivatives such as pentoxifylline, denbufylline, and theophylline inhibit PDE4 and have received considerable attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an antidepressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799–807 for a general review). Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion and stomach erosion.

SUMMARY OF THE INVENTION

The present invention relates to novel compounds, e.g., novel N-substituted aniline and diphenylamine compounds, that inhibit PDE4 enzymes, and especially have improved side effect profiles, e.g., are relatively non-emetic, (e.g., as compared to the previously discussed prior art compounds). Preferably, the compounds selectively inhibit PDE4 enzymes. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, requiring PDE inhibition, especially PDE4 inhibition, for a disease state that involves elevated intracellular PDE 4 levels or decreased cAMP levels, e.g., involving neurological syndromes, especially those states associated with memory impairment, most especially long term memory impairment, as where such memory impairment is due in part to catabolism of intracellular cAMP levels by PDE4 enzymes, or where such memory impairment may be improved by effectively inhibiting PDE4 enzyme activity.

In a preferred aspect, the compounds of the invention improve such diseases by inhibiting PDE4 enzymes at doses which do not induce emesis.

The present invention includes compounds of Formula I:

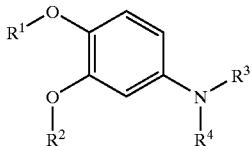

wherein $R^1$ is alkyl having 1 to 4 carbon atoms, which is branched or unbranched and which is unsubstituted or substituted one or more times by halogen (e.g., $CH_3$, $CHF_2$, $CF_3$, etc.);

$R^2$ is alkyl having 1 to 12, preferably 1 to 8 carbon atoms, which is branched or unbranched and which is unsubstituted or substituted one or more times by halogen, hydroxy, cyano, $C_{1-4}$-alkoxy, oxo or combinations thereof, and wherein optionally one or more —$CH_2CH_2$— groups is replaced in each case by —CH=CH— or —C≡C—(e.g., $CH_3$, $CHF_2$, $CF_3$, methoxyethyl, etc.), cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl), cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or combinations thereof (e.g., cyclopentylmethyl, cyclopropylmethyl, etc.), aryl having 6 to 14 carbon atoms, which is unsubstituted or substituted one or more times by halogen, $CF_3$, $OCF_3$, alkyl, hydroxy, alkoxy, nitro, methylenedioxy, ethylenedioxy, cyano, or combinations thereof (e.g., methylphenyl, methoxyphenyl, chlorophenyl, etc.), arylalkyl in which the aryl portion has 6 to 14 carbon atoms and the alkyl portion, which is branched or unbranched, has 1 to 5 carbon atoms, which the arylalkyl radical is unsubstituted or is substituted in the aryl portion one or more times by halogen, $CF_3$, $OCF_3$, alkyl, hydroxy, alkoxy, nitro, cyano, methylenedioxy, ethylenedioxy, or combinations thereof, and wherein in the alkyl portion one or more —$CH_2CH_2$— groups are each optionally replaced by —CH=CH— or —C≡C—, and one or more —$CH_2$— groups are each optionally replaced by —O— or —NH— and/or the alkyl portion is optionally substituted by halogen, oxo, hydroxy, cyano, or combinations thereof (e.g., phenylethyl, phenylpropyl, phenylbutyl, methoxyphenylethyl, methoxyphenylpropyl, chlorophenylethyl, chlorophenylpropyl, phenylethenyl, phenoxyethyl, phenoxybutyl, chlorophenoxyethyl, chlorophenylaminoethyl, etc.), a partially unsaturated carbocyclic group having 5 to 14 carbon atoms, which is unsubstituted or substituted one or more times by halogen, alkyl, alkoxy, hydroxy, nitro, cyano, oxo, or combinations thereof (e.g., cyclohexenyl, cyclohexadienyl, indanyl, tetrahydronaphthenyl, etc.), a heterocyclic group, which is saturated, partially saturated or unsaturated, having 5 to 10 ring atoms in which at least 1 ring atom is a N, O or S atom, which is unsubstituted or substituted one or more times by halogen, hydroxy, aryl, alkyl, alkoxy, cyano, trifluoromethyl, nitro, oxo, or combinations thereof (e.g., 3-thienyl, 3-tetrahydrofuranyl, 3-pyrrolyl, etc.), or a heterocycle-alkyl group, wherein the heterocyclic portion is saturated, partially saturated or unsaturated, and has 5 to 10 ring atoms in which at least 1 ring atom is a N, O or S atom, and the alkyl portion is branched or unbranched and has 1 to 5 carbon atoms, the heterocycle-alkyl group is unsubstituted or substituted one or more times in the heterocyclic portion by halogen, $OCF_3$, hydroxy, aryl, alkyl, alkoxy, cyano, trifluoromethyl, nitro, oxo, or combinations thereof, wherein in the alkyl portion one or more —$CH_2CH_2$— groups are each optionally replaced by —CH=CH— or —C≡C—, and one or more —$CH_2$— groups are each optionally replaced by —O— or —NH— and/or the alkyl portion is optionally substituted by halogen, oxo, hydroxy, cyano, or combinations thereof (e.g., pyridylethyl, pydridylpropyl, methylpiperazinylethyl, etc.);

$R^3$ is H, alkyl having 1 to 8, preferably 1 to 4 carbon atoms, which is branched or unbranched and which is unsubstituted or substituted one or more times with halogen, cyano, $C_{1-4}$-alkoxy, or combinations thereof (e.g., methyl, ethyl, propyl, etc.), a partially unsaturated carbocycle-alkyl group wherein the carbocyclic portion has 5 to 14 carbon atoms and the alkyl portion which is branched or unbranched has 1 to 5 carbon atoms, and which is unsubstituted or substituted in the carbocyclic portion one or more times by halogen, alkyl, alkoxy, nitro, cyano, oxo, or combinations thereof, and the alkyl portion is optionally substituted by halogen, $C_{1-4}$-alkoxy, cyano or combinations thereof (e.g., cyclohexenylmethyl, etc.), arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, alkylamino, dialkylamino and/or substituted in the alkyl portion by halogen, cyano, or methyl (e.g., benzyl, phenethyl, phenpropyl, methylbenzyl, methoxybenzyl, trfluoromethyl, benzyl, methylenedioxobenzyl, etc.), or heteroarylalkyl group, wherein the heteroaryl portion may be partially or fully saturated and has 5 to 10 ring atoms in which at least 1 ring atom is a N, O or S atom, the alkyl portion, which is branched or unbranched, has 1 to 5 carbon atoms, the heteroarylalkyl group is unsubstituted or substituted one or more times in the heteroaryl portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof (e.g., pyridylmethyl, pyridylpropyl, methylpyridylmethyl, chloropyridylmethyl, dichloropyridylmethyl, thienylmethyl, thiazolylmethyl, quinolinylmethyl, isoquinolinylmethyl, piperidinylmethyl, furanylmethyl, imidazolylmethyl, methylimidazolylmethyl, pyrrolylmethyl, etc.);

$R^4$ is H, aryl having 6 to 14 carbon atoms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl (eg., hydroxymethyl), hydroxamic acid, tetrazole-5-yl, 2(-heterocycle)tetrazole-5-yl (eg., 2-(2-tetrahydropyranyl)tetrazole-5-yl), hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (eg. tert-butyldimethylsilyloxy), $R^5$-L-, or combinations thereof (e.g., substituted or unsubstituted phenyl, naphthyl, and biphenyl, such as phenyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), or heteroaryl having 5 to 10 ring atoms in which at least 1 ring atom is a heteroatom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, trialkylsilyloxy (eg. tert-buyldimethylsilyloxy), $R^5$-L-, or combinations thereof (e.g., pyridyl, thienyl, pyrazinyl, quinolinyl, isoquinolinyl, pyrimidinyl, imidazolyl, thiazolyl, etc.);

$R^5$ is H, alkyl having 1 to 8, preferably 1 to 4 carbon atoms, which is unsubstituted or substituted one or more times with halogen, $C_{1-4}$-alkyl, $C_{1-4}$-alkoxy, oxo, or combinations thereof (e.g., methyl, ethyl, propyl, etc.), alkylamino or dialkylamino wherein each alkyl portion has independently 1 to 8, preferably 1 to 4 carbon atoms (e.g., dimethylamino, etc.), a partially unsaturated carbocycle-alkyl group wherein the carbocyclic portion has 5 to 14 carbon atoms and the alkyl portion has 1 to 5 carbon atoms, which is unsubstituted or substituted, preferably in the carbocyclic portion, one or more times by halogen, alkyl, alkoxy, nitro, cyano, oxo, or combinations thereof (e.g., cyclohexenylmethyl, etc.), cycloalkyl having 3 to 10, preferably 3 to 8 carbon atoms, which is unsubstituted or substituted one or more times by halogen, hydroxy, oxo, cyano, alkoxy, alkyl having 1 to 4 carbon atoms, or combinations thereof (e.g., cyclopentyl), cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, alkyl, alkoxy or combinations thereof (e.g., cyclopentylmethyl, cyclopropylmethyl, etc.), aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, (e.g., substituted or unsubstituted phenyl and naphthyl, methylphenyl, chlorophenyl, fluorophenyl, vinylphenyl, cyanophenyl, methylenedioxophenyl, ethylphenyl, dichlorophenyl, carboxyphenyl, ethoxycarbonylphenyl, dimethylphenyl, hydroxymethylphenyl, nitrophenyl, aminophenyl, etc.), arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, amino, alkylamino, dialkylamino and/or substituted in the alkyl portion by halogen, cyano, or methyl (e.g., benzyl, phenethyl, phenpropyl, methylbenzyl, methoxybenzyl, trfluoromethyl, benzyl, methylenedioxobenzyl, etc.), a heterocyclic group, which is saturated, partially saturated or unsaturated, having 5 to 10 ring atoms in which at least 1 ring atom is a N, O or S atom, which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl (eg., hydroxymethyl), hydroxamic acid, tetrazole-5-yl, hydroxyalkoxy, carboxy, alkoxycarbonyl (e.g., tert-butyloxycarbonyl, ethoxycarbonyl), cyano, acyl, alkylthio, alkylsulfinyl, alkylsulfonyl, phenoxy, or combinations thereof (e.g., pyridyl, thienyl, pyrazinyl, quinolinyl, isoquinolinyl, pyrimidinyl, imidazolyl, thiazolyl, etc.), or a heterocycle-alkyl group, wherein the heterocyclic portion is saturated, partially saturated or unsaturated, and has 5 to 10 ring atoms in which at least 1 ring atom is a N, O or S atom, and the alkyl portion which is branched or unbranched and has 1 to 5 carbon atoms, the heterocycle-alkyl group is unsubstituted or substituted one or more times in the heterocyclic portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof (e.g., pyridylmethyl, pyridylpropyl, methylpridylmethyl, etc.);

L is a single bond or a divalent aliphatic radical having 1 to 8 carbon atoms wherein one or more —$CH_2$— groups are each optionally replaced by —O—, —S—, —$NR^6$—, —$SO_2NH$—, —$NHSO_2$—, —CO—, —$NR^6CO$—, —$CONR^6$—, —NHCONH—, —OCONH, —NHCOO—, —SCONH—, —SCSNH—, or —NHCSNH—(e.g., —O—, $CH_2$—, —CO—, —CO—O—, —O—CO—, —CO—NH—, —NH—CO—, —$CH_2CH_2CH_2$—NH—CO—, —$CH_2$—$CH_2$—O—, —$SO_2$—NH—$CH_2CH_2$—O—, —O—$CH_2CH_2$—O—, —$CH_2$—NH—CO—, —CO—NH—$CH_2$—, —$SO_2$—NH—, —$CH_2$—NH—$SO_2$—, —$CH_2CH_2CH_2$—$SO_2$—NH—, etc.); and $R^6$ is H, alkyl having 1 to 8, preferably 1 to 4 carbon atoms, which is branched or unbranched and which is unsubstituted or substituted one or more times with halogen, $C_{1-4}$-alkyl, $C_{1-4}$-alkoxy, oxo, or combinations thereof (e.g., methyl, ethyl, propyl, etc.);

wherein at least one of $R^3$ and $R^4$ is other than H; and pharmaceutically acceptable salts thereof.

According to a further aspect of the invention there is provided a genus of novel compounds according to the formulas II and III:

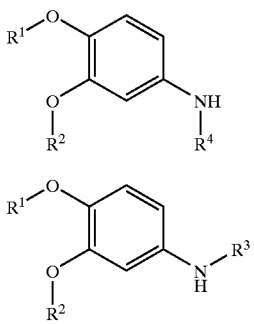

wherein $R^1$, $R^2$, $R^3$, and $R^4$ are as defined above. The compounds of this subgenus of formula I not only have PDE4 inhibitory activity, but also are useful as intermediates for preparing compounds of Formula I in which $R^3$ and $R^4$ are both other than H.

In addition, preferred compounds of formula I are those of the subformula IV

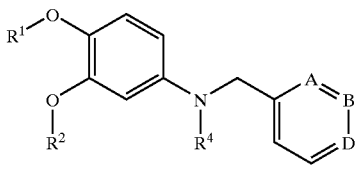

wherein $R^1$, $R^2$, and $R^4$ are as defined in Formula I and one of A, B and D is N and the others are C. Preferably, B is N. Also, $R^4$ is preferably pyridyl or phenyl which in each case is substituted or unsubstituted.

The present invention also includes compounds of Formula I':

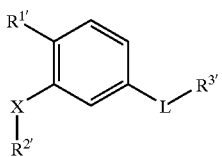

wherein $R^{1'}$ is methoxy, F, Cl, $CHF_2$ or $CF_3$;

$R^{2'}$ is alkyl having 1 to 12 carbon atoms, alkyl having 1 to 12 carbon atoms which is substituted one or more times by halogen, oxo, cyano, or combinations thereof, alkenyl having 2 to 12 carbon atoms, alkenyl having 2 to 12 carbon atoms which is substituted one or more times by halogen, oxo, cyano or combinations thereof, alkynyl having 2 to 12 carbon atoms, alkynyl having 2 to 12 carbon atoms which is substituted one or more times by halogen, oxo, cyano or combinations thereof, cycloalkyl having 3 to 10 carbon atoms, cycloalkyl having 3 to 10 carbon atoms substituted one or more times by halogen, oxo, alkyl, or combinations thereof, cycloalkylalkyl having 4 to 12 carbon atoms, cycloalkylalkyl having 4 to 12 carbon atoms which is substituted one or more times by halogen, oxo, alkyl or combinations thereof, a partially unsaturated carbocyclic group having 5 to 14 carbon atoms, a partially unsaturated carbocyclic group having 5 to 14 carbon atoms which is substituted one or more times by halogen, alkyl, alkyloxy, nitro, cyano, oxo, or combinations thereof, arylalkyl having 7 to 26 carbon atoms arylalkyl having 7 to 26 carbon atoms which is substituted one or more times by halogen, alkyl, alkoxy, nitro, cyano, oxo, trifluoromethyl, or combinations thereof, heteroarylalkyl having 5 to 10 ring atoms in which at least 1 ring atom is a heteroatom, or substituted heteroarylalkyl having 5 to 10 ring atoms in which at least 1 ring atom is a heteroatom and which is substituted one or more times in the heteroaryl portion by halogen, aryl, alkyl, alkoxy, cyano, trifluoromethyl, nitro, amino, alkylamino, dialkylamino or combinations thereof and/or substituted in the alkyl portion by halogen, oxo, cyano, or combinations thereof;

X is O or S;

$R^{3'}$ is aryl having 6 to 14 carbon atoms, aryl having 6 to 14 carbon atoms which is substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy, heteroaryl which is unsubstituted or substituted by halogen, alkyl or alkoxy, or combinations thereof, heteroaryl having 5 to 10 ring atoms in which at least 1 ring atom is a heteroatom, or substituted heteroaryl having 5 to 10 ring atoms in which at least 1 ring atom is a heteroatom which is substituted one or more times by halogen, aryl, alkyl, alkoxy, cyano, trifluoromethyl, nitro, oxo, amino, alkylamino, dialkylamino or combinations thereof;

L is —NH—, —$NR^{4'}$—, —$NHCH_2$—, —$NR^{4'}CH_2$—, or —$CH_2NR^{4'}$—; and $R^{4'}$ is alkyl having 1 to 12 carbon atoms, alkyl having 1 to 12 carbon atoms which is substituted one or more times by halogen, oxo, cyano, or combinations thereof, aryl having 6 to 14 carbon atoms and which is unsubstituted or substituted one or more times by halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, phenoxy or combinations thereof, heteroaryl having 5 to 10 ring atoms in which at least 1 ring atom is a heteroatom, substituted heteroaryl having 5 to 10 ring atoms in which at least 1 ring atom is a heteroatom and which is substituted one or more times by halogen, aryl, alkyl, alkoxy, cyano, trifluoromethyl, nitro, oxo, amino, alkylamino, dialkylamino or combinations thereof, arylalkyl having 7 to 16 carbon atoms, arylalkyl having 7 to 16 carbon atoms which is substituted one or more times by halogen, alkyl, alkoxy, nitro, cyano, oxo, trifluoromethyl, or combinations thereof, heteroarylalkyl having 5 to 10 ring atoms in which at least 1 ring atom is a heteroatom, or substituted heteroarylalkyl having 5 to 10 ring atoms in which at least 1 ring atom is a heteroatom and which is substituted one or more times in the heteroaryl portion by halogen, aryl, alkyl, alkoxy, cyano, trifluoromethyl, nitro, oxo, amino, alkylamino, dialkylamino or combinations thereof and/or substituted in the alkyl portion by halogen, oxo, cyano, or combinations thereof; and pharmaceutically acceptable salts thereof.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes but is not limited to inflammatory diseases. These compounds may also function as antidepressants, or be useful in treating cognitive and negative symptoms of schizophrenia.

Assays for determining PDE inhibiting activity as well as selectivity of PDE 4 inhibiting activity and selectivity of inhibiting PDE 4 isoenzymes are known within the art. See, e.g., U.S. Pat. No. 6,136,821, the disclosure of which is incorporated herein by reference.

According to a further aspect of the invention there are provided compounds useful as intermediates for the production of the PDE4 inhibitors described herein (e.g., PDE4 inhibitors of Formula I) and/or useful for the synthesis of radio-labeled analogs of the PDE4 inhibitors with in this application.

Thus, there are provided intermediate compounds which correspond to compounds of Formula I, wherein $R^2$, $R^3$, and $R^4$ are as previously defined for Formula I, but $R^1$ is H, tert-butyldimethylsilyl-, or a suitable phenolic protecting group. Suitable phenolic protecting groups are described, for example, in Greene, T. W. and Wuts, P. G. M., Protective Groups in Organic Synthesis, $3^{rd}$ Edition, John Wiley & Sons, 1999, pp. 246–293. These intermediates are also useful for the synthesis of radio-labeled compounds, such as where $R^1$ is $^3H_3C$—, $^{14}CH_3$— or $^{11}CH_3$—, for example by removing the protecting group and reacting the resultant compound in which $R^1$ is H with suitable radio-labelled reagents. Such radio-labeled compounds are useful for determining compound tissue distribution in animals, in PET imaging studies, and for in vivo, ex vivo, and in vitro binding studies.

Also provided are intermediate compounds which correspond to compounds of Formula I, wherein $R^1$, $R^3$, and $R^4$ are as previously defined for Formula I, but $R^2$ is H, tert-butyldimethylsilyloxy-, or a suitable phenolic protecting group. Suitable phenolic protecting groups are described, for example, in Greene, T. W. and Wuts, P. G. M., Protective Groups in Organic Synthesis, $3^{rd}$ Edition, John Wiley & Sons, 1999, pp. 246–293. Compounds in which $R^2$ is H are useful as intermediates, for example, as scaffolds for parallel or combinatorial chemistry applications. Further, these compounds are useful for the introduction of radio-labels such as $^3H$, $^{14}C$, or $^{11}C$.

As previously described, compounds according to formula II, wherein $R^1$, $R^2$ and $R^4$ are as previously described are useful intermediates for the production of compounds according to formula I where in $R^3$ is other than H.

Also, as previously described, compounds according to formula III, wherein $R^1$, $R^2$ and $R^3$ are as previously described are useful intermediates for the production of compounds according to formula I where in $R^4$ is other than H.

Halogen herein refers to F, Cl, Br, and I. Preferred halogens are F and Cl.

Alkyl, as a group or substituent per se or as part of a group or substituent (e.g., alkylamino, trialkylsilyloxy, aminoalkyl, hydroxyalkyl), means a straight-chain or branched-chain aliphatic hydrocarbon radical having 1 to 12 carbon atoms, preferably 1 to 8 carbon atoms, especially 1 to 4 carbon atoms. Suitable alkyl groups include methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by halogens, oxo, hydroxyl, $C_{1-4}$-alkoxy and/or cyano. Halogens are preferred substituents, especially F and Cl.

Alkoxy means alkyl-O-groups and alkoxyalkoxy means alkyl-O-alkyl-O-groups in which the alkyl portions are in accordance with the previous discussion. Suitable alkoxy and alkoxyalkoxy groups include methoxy, ethoxy, propoxy, butoxy, pentoxy, hexoxy, heptoxy, octoxy methoxymethoxy ethoxymethoxy, propoxymethoxy, and methoxyethoxy. Preferred alkoxy groups are methoxy and ethoxy. Similarly, alkoxycarbonyl means alkyl —O—CO— in which the alkyl portion is in accordance with the previous discussion. Examples include methoxycarbonyl, ethoxycarbonyl, propoxycarbonyl, and tert-butoxycarbonyl.

Cycloalkyl means a monocyclic, bicyclic or tricyclic nonaromatic saturated hydrocarbon radical having 3 to 10 carbon atoms, preferably 3 to 8 carbon atoms, especially 3 to 6 carbon atoms. Suitable cycloalkyl groups include cyclopropyl, cyclobutyl, cyclopentyl, cyclohexyl, cycloheptyl, cyclooctyl, norbomyl, 1-decalin, adamant-1-yl, and adamant-2-yl. Other suitable cycloalkyl groups include spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, and spiro[3.5]nonyl. Preferred cycloalklyl groups are cyclopropyl, cyclopentyl and cyclohexyl. The cycloalkyl group can be substituted, for example, substituted by halogens and/or alkyl groups.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulfinyl, alkylsulfonyl, and phenoxy.

Arylalkyl refers to an aryl-alkyl-radical in which the aryl and alkyl portions are in accordance with the previous descriptions. Suitable examples include benzyl, 1-phenethyl, 2-phenethyl, phenpropyl, phenbutyl, phenpentyl, and napthylmethyl.

Heteroaryl refers to an aromatic heterocyclic group having one or two rings and a total number of 5 to 10 ring atoms wherein at least one of the ring atoms is a heteroatom. Preferably, the heteroaryl group contains 1 to 3, especially 1 or 2, hetero-ring atoms which are selected from N, O and S. Suitable heteroaryl groups include furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, e.g., 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7-, or 8-isoquinolinyl.

Substituted heteroaryl refers to the heteroaryl groups described above which are substitued in one or more places by, for example, halogen, aryl, alkyl, alkoxy, carboxy, methylene, cyano, trifluoromethyl, nitro, oxo, amino, alkylamino, and dialkylamino.

Heterocycles include heteroaryl groups as described above as well as non-aromatic cyclic groups containing at least one hetero-ring atom, preferably selected from N, S and O, for example, tetrahydrofuranyl, piperidinyl, and pyrrolidinyl.

Heterocycle-alkyl refers to a heterocycle-alkyl-group wherein the heterocyclic and alkyl portions are in accordance with the previous discussions. Suitable examples are pyridylmethyl, thienylmethyl, pyrimidinylmethyl, pyrazinylmethyl, and isoquinolinylmethyl.

Partially unsaturated carbocyclic structures are non-aromatic monocyclic or bicyclic structures containing 5 to 14 carbon atoms, preferably 6 to 10 carbon atoms, wherein the ring structure(s) contains at least one C=C bond. Suitable examples arecyclopentenyl, cyclohexenyl, cyclohexadienyl, tetrahydronaphthenyl and indan-2-yl.

Alkenyl refers to straight-chain or branched-chain aliphatic radicals containing 2 to 12 carbon atoms in which one or more —CH$_2$—CH$_2$— structures are each replaced by —CH=CH—. Suitable alkenyl groups are ethenyl, 1-propenyl, 2-methylethenyl, 1-butene, 2-butene, 1-pentenyl, and 2-pentenyl.

Alkynyl refers to straight-chain or branched-chain aliphatic radicals containing 2 to 12 carbon atoms in which one or more —CH$_2$—CH$_2$— structures are each replaced by —C≡C—. Suitable alkynyl groups are ethynyl, propynyl, 1-butynyl, and 2-butynyl.

Acyl refers to alkanoyl radicals having 1 to 13 carbon atoms in which the alkyl portion can be substituted by halogen, alkyl, aryl and/or alkoxy, or aroyl radicals having 7 to 15 carbon atoms in which the aryl portion can be substituted by, for example, halogen, alkyl and/or alkoxy. Suitable acyl groups include formyl, acetyl, propionyl, butanoyl and benzoyl.

Substituted radicals preferably have 1 to 3 substituents, especially 1 to 2 substituents.

In the compounds of Formula I, $R^1$ is an alkyl group having preferably 1 to 4 carbon atoms which is optionally substituted by halogen, preferably fluorine or chlorine. In particular, $R^1$ is preferably methyl or difluoromethyl.

$R^2$ is preferably cycloalkyl, particularly cyclopentyl.

$R^2$ is also preferably aryl or arylalkyl, particularly substituted or unsubstituted phenyl or phenylalkyl, such as phenyl, methylphenyl, methoxyphenyl, chlorophenyl, phenethyl, phenpropyl, phenbutyl, phenylethenyl, phenoxyethyl, phenoxypropyl, phenoxybutyl, chlorophenylethyl, methoxyphenyl ethyl, chlorophenylethenyl, chlorophenoxyethyl, chlorophenypropyl, methoxyphenpropyl, methoxyphenbutyl, chlorophenbutyl, nitrophenbutyl, chlorophenylaminoethyl, and the like, $R^2$ is also preferably a partially unsaturated carbocyclic groups, which is unsubstituted or substituted, particularly cyclohexenyl, cyclohexadienyl, indan-2-yl.

$R^2$ is also preferably an alkyl group having 1 to 8 carbon atoms, especially 1 to 4 carbon atoms, which is substituted or unsubstituted, e.g., methyl, difluoromethyl, trifluoromethyl, and methoxyethyl.

$R^2$ is also preferably a heterocyclic or heterocycle—alkyl group, particularly radicals in which the heterocyclic group has 5 to 6 ring atoms and 1 to 2 hetero-ring atoms selected from N, O and S, e.g., tetrahydrofuranyl, pyrrolidinyl, pyrrolyl, pyridylmethyl, pyridylethyl, pyridylpropyl, piperazinylmethyl, piperazinylethyl, methylpiperazinylethyl and the like.

Preferred $R^2$ include cyclopentyl, tetrahydrofuranyl, $CHF_2$, methoxyethyl, cyclopropylmethyl, phenethyl, phenpropyl, phenylethenyl, phenoxyethyl, phenoxybutyl, phenylaminoethyl, indan-2-yl, pyridylethyl, and pyridylpropyl.

$R^3$ is preferably hydrogen, alkyl having 1 to 4 carbon atoms (e.g., methyl, ethyl, n-propyl, or n-butyl), arylalkyl (e.g., substituted or unsubstitituted benzyl, phenethyl, and phenpropyl), or a heteroarylalkyl group (e.g., substituted or unsubstituted pyridylmethyl, furanylmethyl, thienylmethyl, pyrrolylmethyl, pyrimidinylmethyl, thiazolylmethyl, isoquinolinylmethyl and quinolinylmethyl). Preferred substituents for aryl and heteroaryl portions of $R^3$ are F, Cl, $CH_3$, $C_2H_5$, $OCH_3$, and CN.

$R^4$ is preferably aryl, or heteroaryl, especially phenyl, naphthyl, biphenyl, furanyl, pyrazinyl, pyrimidinyl, pyridyl, quinolinyl, and isoquinolinyl, which in each case is unsubstituted or is substituted one or more times. Preferred substituents are OH, F, Cl, $CF_3$, alkyl (such as methyl or ethyl), alkoxy (such as methoxy and ethoxy), CN, vinyl, $CH_2OH$, CONHOH, $CONH_2$, methylenedioxy, COOH, and combinations thereof.

In addition, when $R^4$ is aryl, especially, phenyl, preferred substituents include $R^5$—L—, e.g., $R^5$—, $R^5$—O—, $R^5$—CO—, $R^5$—NH—CO—, $R^5$—SO$_2$—NH—, $R^5$—SO$_2$—NH-alkylene-O—, NH2—alkyl-NH—CO—, $R^5$-alkylene-NH—CO—, alkyl-CO—NH-alkyl- as well as methyl, ethyl, Cl, F, CN, $OCH_3$, $CF_3$, amino, nitro, $HOCH_2$ and COOH.

When $R^4$ is aryl substituted by $R^5$—SO$_2$—NH— it is preferably a substituted phenyl group and $R^5$ is preferably methyl, ethyl, propyl or phenyl.

When $R^4$ is aryl substituted by $R^5$—SO$_2$—NH-alkylene-O— it is preferably a substituted phenyl. In such cases, $R^5$ is preferably methyl, ethyl, propyl or phenyl and alkylene is preferably —CH$_2$—, —CH$_2$CH$_2$— or —CH$_2$CH$_2$CH$_2$—.

When $R^4$ is aryl substituted by $R^5$—L— it is preferably substituted phenyl. In such cases, preferred $R^5$ groups include tetrazolyl, oxazinyl, piperazinyl, methylpiperazinyl, pyridyl, methylpyridyl, pyrrolinyl, methylpyrrolinyl, piperadinyl, or methylpiperadinyl, and L is preferably a single bond, —O—, —CO—, —CH$_2$—, —CH$_2$CH$_2$—, —CH$_2$CH$_2$CH$_2$—, —CH$_2$—O—, —CH$_2$CH$_2$—O—, —CH$_2$CH$_2$CH$_2$—O—, —CH$_2$—NH—CH$_2$CH$_2$—O—, —CO—NH— or —NH—CO—.

In addition, preferred PDE4 inhibitors in accordance with the invention are compounds described by subformulas Ia–Ih which correspond to formula I but exhibit the following preferred groups:

Ia $R^1$ is methyl or CHF$_2$; $R^2$ is alkyl, alkenyl, alkynyl, cycloalkyl, arylalkyl, heterocycle-alkyl, cycloalkylalkyl, aryl, or heterocyclic, in each case substituted or unsubstituted; $R^3$ is H, alkyl, arylalkyl or heteroarylalkyl, in each case substituted or unsubstituted; and $R^4$ is aryl or heteroaryl, in each case substituted or unsubstituted.

Ib $R^3$ is heteroarylalkyl which is substituted or unsubstituted.

Ic $R^1$ is methyl or CHF$_2$; and $R^2$ is cyclopentyl, CHF$_2$, cyclopropylmethyl, pyridylethyl (particularly 2-pyridylethyl), or tetrahydrofuranyl (particularly (3R)-tetrahydrofuranyl).

Id $R^1$ is methyl or CHF$_2$; $R^2$ is cyclopentyl; $R^3$ is heteroarylalkyl, in each case substituted or unsubstituted; and $R^4$ is substituted or unsubstituted aryl or heteroaryl.

Ie $R^1$ is methyl; $R^2$ is cyclopentyl; and $R^3$ is heteroarylalkyl which is substituted or unsubstituted.

If $R^1$ is methyl; $R^2$ is cyclopentyl; $R^3$ is heteroarylalkyl which is substituted or unsubstituted; and $R^4$ is phenyl which is substituted or unsubstituted.

Ig $R^1$ is methyl; $R^2$ is cyclopentyl; $R^3$ is pyridylmethyl, phenethyl, benzyl, thienylmethyl, pyridylpropyl, piperidinylmethyl, or pyrazinylmethyl, which in each case is substituted or unsustituted, or methyl, ethyl, or propyl; and $R^4$ is phenyl or phenyl substituted with 1 to 3 substituents.

Ih $R^1$ is methyl; $R^2$ is cyclopentyl; $R^3$ is pyridylmethyl, phenethyl, benzyl, thienylmethyl, pyridylpropyl, piperidinylmethyl, pyrazinylmethyl, which in each case is substituted or unsustituted, or methyl, ethyl, or propyl; and $R^4$ is phenyl, naphthyl, biphenyl, pyridyl, pyrimidinyl, thiazolyl, pyrazinyl, quinolinyl, or isoquinolinyl, in each case substituted or unsubstituted.

In addition, preferred PDE4 inhibitors in accordance with the invention are compounds described by subformulas IIa–IId which correspond to formula II but exhibit the following preferred groups:

IIa $R^1$ is methyl or CHF$_2$; $R^2$ is cyclopentyl, CHF$_2$, cyclopropylmethyl, pyridylethyl (particularly 2-pyridylethyl), or tetrahydrofuranyl (particularly (3R)-tetrahydrofuranyl); and $R^4$ is phenyl, naphthyl, pyridyl, quinolinyl, or isoquinolinyl, which in each case is substituted or unsubstituted.

IIb $R^1$ is methyl or CHF$_2$; $R^2$ is cyclopentyl, CHF$_2$, cyclopropylmethyl, pyridylethyl (particularly 2-pyridylethyl), or tetrahydrofuranyl (particularly (3R)-tetrahydrofuranyl); and $R^4$ is phenyl which is unsubstituted or substituted by methyl, ethyl, methoxy, Cl, F, CF$_3$, vinyl, cyano, amino, carboxy, hydroxymethyl, or ethylsulfonamido, or is 3-pyridyl which is unsubstituted or substituted by carboxy or alkoxycarbonyl.

IIc $R^1$ is methyl; $R^2$ is cyclopentyl; and $R^4$ is phenyl, naphthyl, pyridyl, quinolinyl, or isoquinolinyl, which in each case is substituted or unsubstituted.

IId $R^1$ is methyl; $R^2$ is cyclopentyl; and $R^4$ is phenyl which is unsubstituted or substituted by methyl, ethyl, methoxy, Cl, F, CF$_3$, vinyl, cyano, amino, carboxy, hydroxymethyl, or ethylsulfonamido, or is 3-pyridyl which is unsubstituted or substituted by carboxy or alkoxycarbonyl.

In addition, preferred PDE4 inhibitors in accordance with the invention are compounds described by subformulas IIIa–IIId which correspond to formula III but exhibit the following preferred groups:

IIIa $R^1$ is methyl or CHF$_2$; $R^2$ is cyclopentyl, CHF$_2$, cyclopropylmethyl, pyridylethyl (particularly 2-pyridylethyl), or tetrahydrofuranyl (particularly (3R)-tetrahydrofuranyl); and $R^3$ is benzyl, phenethyl, cyclohexenyhnethyl, furanylmethyl, thienylmethyl, pyridylmethyl, quinolinymethyl, isoquinolinylmethyl, thiazolylmethyl, or pyrrolylmethyl, which in each case is substituted or unsubstituted.

IIIb $R^1$ is methyl or CHF$_2$; $R^2$ is cyclopentyl, CHF$_2$, cyclopropylmethyl, pyridylethyl (particularly 2-pyridylethyl), or tetrahydrofuranyl (particularly (3R)-tetrahydrofuranyl); and $R^3$ is pyrazinylmethyl, pyrimidinylmethyl or pyridylmethyl, which in each is unsubstituted or substituted.

IIIc $R^1$ is methyl; $R^2$ is cyclopentyl; and $R^3$ is benzyl, phenethyl, cyclohexenylmethyl, furanylmethyl, thienylmethyl, pyrazinylmethyl, pyrimidinylmethyl, pyridylmethyl, quinolinymethyl, isoquinolinylmethyl, isoimidazolyl, thiazolylmethyl, or pyrrolylmethyl, which in each case is substituted or unsubstituted.

IIId $R^1$ is methyl; $R^2$ is cyclopentyl; and $R^3$ is pyrazinylmethyl or pyridylmethyl, which in each is unsubstituted or substituted.

In addition, preferred PDE4 inhibitors in accordance with the invention are compounds described by subformulas IVa–IVp which correspond to formula IV but exhibit the following preferred groups:

IVa $R^1$ is methyl or CHF$_2$.

IVb $R^1$ is methyl or CHF$_2$, and B is N.

IVc $R^1$ is methyl or CHF$_2$, and $R^2$ is cyclopentyl, CHF$_2$, cyclopropylmethyl, pyridylethyl (particularly 2-pyridylethyl), or tetrahydrofuranyl (particularly (3R)-tetrahydrofuranyl).

IVd $R^1$ is methyl or CHF$_2$, B is N, and $R^2$ is cyclopentyl, CHF$_2$, cyclopropylmethyl, pyridylethyl (particularly 2-pyridylethyl), or tetrahydrofuranyl (particularly (3R)-tetrahydrofuranyl).

IVe $R^1$ is methyl or CHF$_2$, and $R^4$ is 3-pyridyl or phenyl, which in each case is substituted or unsubstituted.

IVf $R^1$ is methyl or CHF$_2$, B is N, and $R^4$ is 3-pyridyl or phenyl, which in each case is substituted or unsubstituted.

IVg $R^1$ is methyl or CHF$_2$, $R^2$ is cyclopentyl, CHF$_2$, cyclopropylmethyl, pyridylethyl (particularly 2-pyridylethyl), or tetrahydrofuranyl (particularly (3R)-tetrahydrofuranyl), and $R^4$ is 3-pyridyl or phenyl, which in each case is substituted or unsubstituted.

IVh $R^1$ is methyl or CHF$_2$, B is N, $R^2$ is cyclopentyl, CHF$_2$, cyclopropylmethyl, pyridylethyl (particularly 2-pyidylethyl), or tetrahydrofuranyl (particularly (3R)-tetrahydrofuranyl), and $R^4$ is 3-pyridyl or phenyl, which in each case is substituted or unsubstituted.

IVi $R^1$ is methyl or CHF$_2$, and $R^4$ is phenyl which is substituted in the 3- or 4-position.

IVj $R^1$ is methyl or CHF$_2$, B is N, and $R^4$ is phenyl which is substituted in the 3- or 4-position.

IVk $R^1$ is methyl or $CHF_2$, $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and $R^4$ is phenyl which is substituted in the 3- or 4-position.

IVl $R^1$ is methyl or $CHF_2$, B is N, $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and $R^4$ is phenyl which is substituted in the 3- or 4-position.

IVm $R^1$ is methyl or $CHF_2$, and $R^4$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

IVn $R^1$ is methyl or $CHF_2$, B is N, and $R^4$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

IVo $R^1$ is methyl or $CHF_2$, $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and $R^4$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

IVp $R^1$ is methyl or $CHF_2$, B is N, $R^2$ is cyclopentyl, $CHF_2$, cyclopropylmethyl, pyridylethyl (particularly 2-pyridylethyl), or tetrahydrofuranyl (particularly (3R)-tetrahydrofuranyl), and $R^4$ is 3-pyridyl, 3-COOH-phenyl, 3-Cl-phenyl, 3-cyano-phenyl, 3-ethylsulfonamido-phenyl, 3-tetrazol-5-yl-phenyl, 3-hydroxymethyl-phenyl, 3-nitro-phenyl, 4-pyridyl, 4-COOH-phenyl, 4-cyano-phenyl, 4-ethylsulfonamido-phenyl, 4-tetrazol-5-yl-phenyl, or 4-hydroxymethyl-phenyl.

Preferred aspects include pharmaceutical compositions comprising a compound of this invention and a pharmaceutically acceptable carrier and, optionally, another active agent as discussed below; a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating neurological syndrome, e.g., loss of memory, especially long-term memory, cognitive impairment or decline, memory impairment, etc. a method of treating a disease state modulated by PDE4 activity, in a mammal, e.g., a human, e.g., those mentioned herein.

The compounds of the present invention may be prepared conventionally. Some of the processes which can be used are described below. All starting materials are known or can be conventionally prepared from known starting materials.

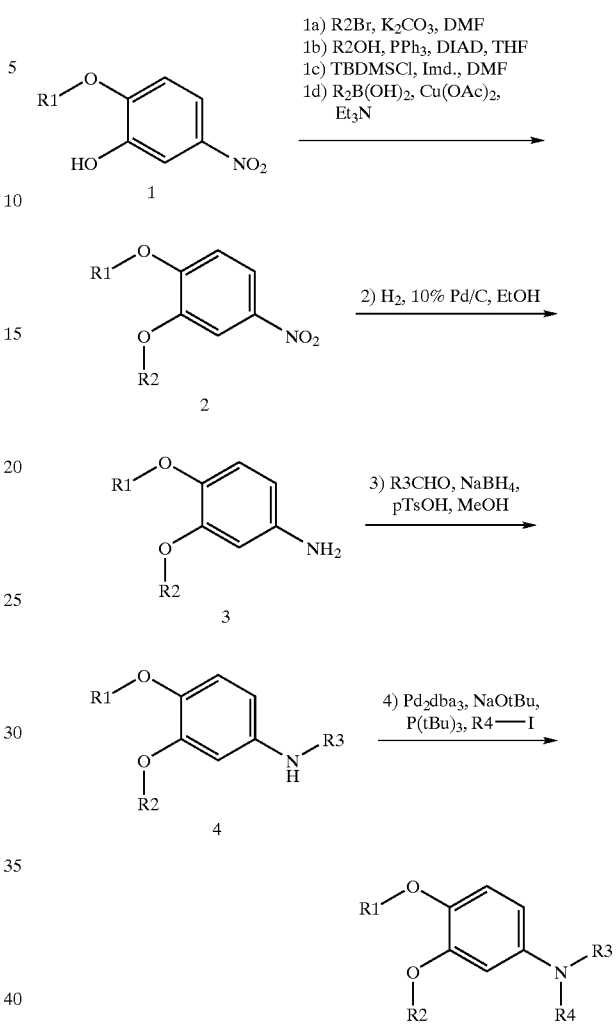

Starting nitrophenols of the type 1 are either commercially available (e.g., R1=$CH_3$) or prepared by published procedures (e.g., R1=$CHF_2$ or both R1 and R2=$CHF_2$, see Mueller, Klaus-Helmut. Eur. Pat. Appl. (1994), 8 pp. CODEN: EPXXDW EP 626361A1; Touma, Toshihiko; Asai, Tomoyuki. Jpn. Kokai Tokkyo Koho (1999), 6 pp. CODEN: JKXXAF JP 11071319 A2; Platonov, Andrew; Seavakov, Andrew; Maiyorova, Helen; Chistokletov, Victor. Int. Symp. Wood. Pulping Chem., 1995, 8th, 3, 295–299; Christensen, Siegfried Benjamin; Dabbs, Steven; Karpinski, Joseph M. PCT Int. Appl. (1996), 12 pp. CODEN: PIXXD2 WO 9623754 A119960808). Aniline intermediates 3 are produced in two steps; first, an addition reaction provides intermediate 2, followed by reduction of the nitro group. Intermediate nitro compounds 2 can be prepared by numerous published procedures, such as by Mitsunobu reactions or standard alkylation reactions. Compounds where R2 is aryl or heteroaryl can be prepared by copper catalyzed reactions with aryl or heteroaryl iodides under Ullman conditions or by coupling aryl-, vinyl-, or heteroaryl-boronic acids with phenol 2 in the presence of a copper catalyst (e.g., Cu(OAc)$_2$) and base such as TEA. Mitsunobu reaction between an appropriately substituted nitrophenol and a primary or secondary alcohol using an azodicarboxylate (e.g., DEAD, DIAD), and a suitable phosphine (e.g., Ph₃P, Bu₃P) provides alkylated nitrophenols 2. Mitsunobu reactions are general performed in aprotic solvents such as dichloromethane or THF. Alternatively, alkylation can be achieved by the reaction between an appropriately substituted nitrophenol and an alkyl halide in the presence of a base (e.g., $K_2CO_3$ or NaH) in a polar aprotic solvent (e.g., DMF or $CH_3CN$).

Nitrocatechols 2 are subsequently reduced to the corresponding anilines 3 by methods standard in the art such as by hydrogenation using a suitable catalyst (e.g., Pd on carbon) in a polar protic solvent (e.g., MeOH or EtOH) under an atmosphere of hydrogen. Alternatively, nitrocatechols 3 can be reduced by using a hydride source (e.g., $NaBH_4$) and a transition metal catalyst (e.g., $NiCl_2$, Pd on carbon) or by using metals (e.g., Zn, Sn, Fe) in mineral acid solutions (e.g., HCl) to produce the corresponding anilines. Generally polar protic solvents such as ethanol or methanol are used in these reactions.

N-Arylalkylanilines 4 are synthesized by standard methods in the art such as by reductive amination reaction, alkylation reaction, or by reduction of corresponding amides. For example, the reductive amination reaction of an aryl or arylalkyl aldehyde with appropriately substituted anilines in the presence of a borohydride reducing agent such as $NaBH_4$ or $NaBH_3CN$ with an acid catalyst such as acetic acid or pTsOH provides desired N-arylalkylanilines. These reactions generally take place in polar protic solvents such as methanol, ethanol, isopropanol, n-propanol and the like.

N-Arylalkylanilines 4 readily undergo N-arylation by methods standard to the art including Ullman coupling reaction, metal-catalyzed coupling, or aromatic nucleophilic substitution reaction. For example, the metal catalyzed reaction between an N-benzylaniline and an aryl halide using a palladium catalyst, (e.g., $Pd_2dba_3$), a bulky electron rich phosphine ligand (e.g., tributylphosphine), and suitable base (e.g., NaOtBu) provides N-Arylalkyldiphenylamines. Nickel and copper catalysts have been employed as well. Solvents useful in this reaction include non-polar aprotic solvents such as toluene, benzene, xylenes, tetrahydrofuran, and ether. When synthesizing compounds of the type 5 wherein R4 is an alkoxycarbonylphenyl, it is advantageous that amine 4 is coupled with 1.1 equivalents of tert-butyl 3-iodobenzene and that 22 mol % of $(tBu)_3P$, 5.5 mol % of $Pd_2(dba)_3$ and 1.3 equivalents of tBuONa are used.

SCHEME 2

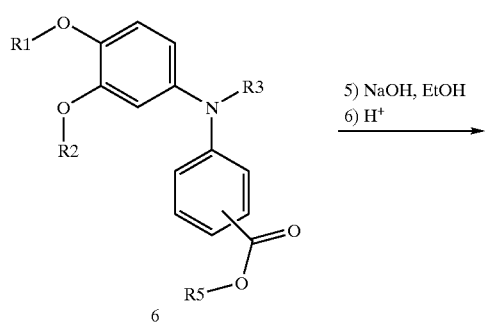

6

5) NaOH, EtOH
6) H⁺

-continued

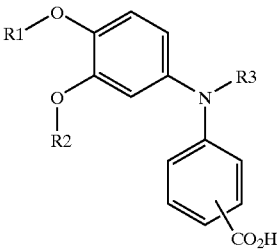

7

Carboxylic ester intermediates 6 can be hydrolyzed under acidic or basic conditions to give the corresponding carboxylic acids 7. For example, an ethyl ester (R5=Et) can be hydrolyzed using a mixture of aqueous base (e.g., NaOH, KOH) and a water miscible solvent (e.g., EtOH, THF). While t-Butyl esters (R5=t-butyl) can be hydrolyzed using an aqueous acid (e.g., HCl, formic acid, TFA) in a water miscible organic solvent, if necessary.

SCHEME 3

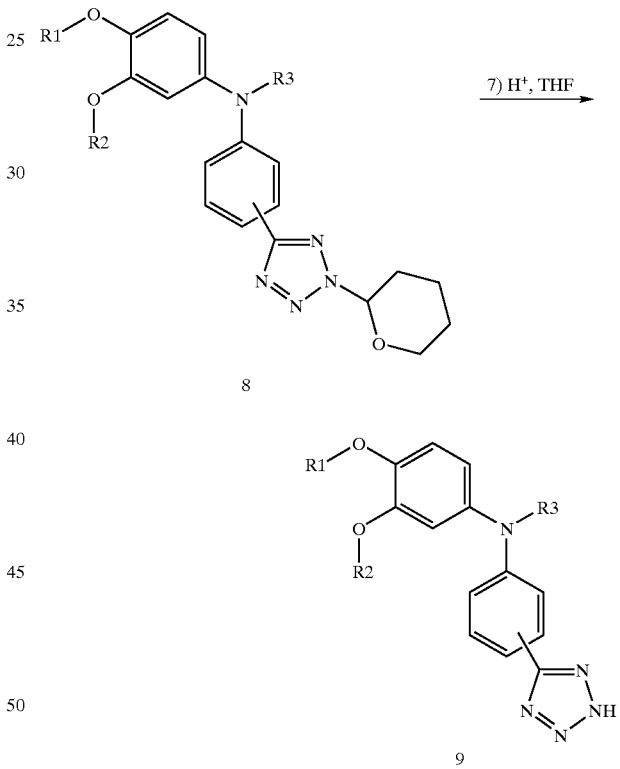

7) H⁺, THF

Coupling of protected tetrazole bromo or iodobenzenes (e.g., 5-(3-iodophenyl)-2-(2-tetrahydropyran)tetrazole) with N-substituted aniline derivatives 4 produce THP-protected tetrazoles 8. Hydrolysis of THP-protected tetrazoles 8 can be accomplished by using an aqueous acid, such as HCl in water and a miscible solvent such as THF or EtOH to provide tetrazoles 9. Further, THP tetrazoles 8 can also be oxidatively cleaved using reagents such as CAN and DDQ in halognenated hydrocarbon solvents such as dichloromethane, chloroform, dichloroethane and the like to yield tetrazoles 9.

Alternatively, tetrazole analogs 9 can be prepared from the corresponding nitriles by treatment with azide ion (e.g., $KN_3$, $NaN_3$, etc.) and a proton source (e.g., $NH_4Cl$) in a polar aprotic solvent such as DMF. They also may be prepared by treatment with an azide ion and a Lewis acid (e.g., ZnBr$_2$) in water, using a water miscible co-solvent such as isopropanol if necessary. Another method of preparation is by treatment of a nitrile with tin or silicon azides (e.g., Me$_3$SiN$_3$, Bu$_3$SnN$_3$) in an aprotic organic solvent such as benzene, toluene, dichloromethane, dichloroethane, ether, THF, and the like.

dichloropyridine, and 4-(bromomethyl)-benzoic acid, or salts thereof, in the presence of a non-nucleophilic base such as sodium hydride, potassium hexamethyldisilazide or potassium diisopropylamide to provide N-substituted diphenylamines 5. Solvents useful in this reaction include aprotic solvents such as benzene, toluene, tetrahydrofuran, ether, DMF, and the like.

SCHEME 4

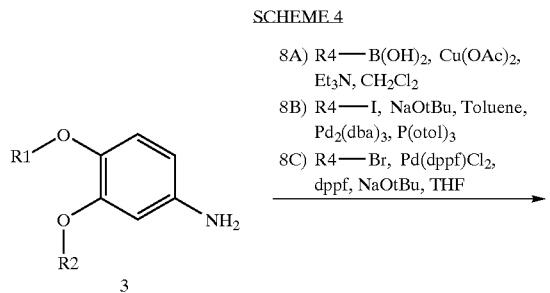

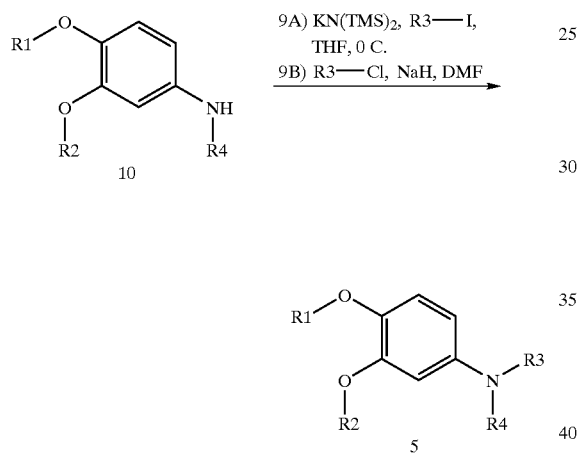

SCHEME 5

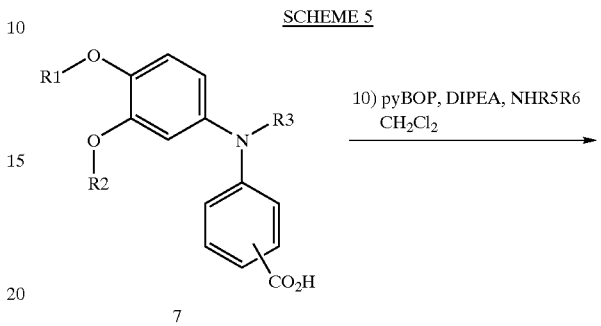

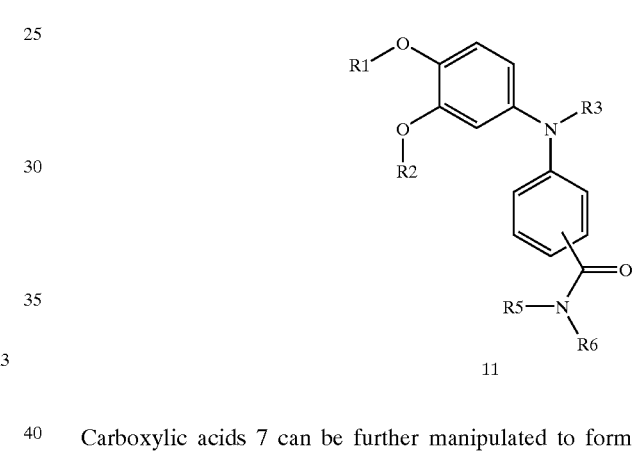

Diphenylamines 10 can be prepared by coupling appropriately substituted anilines 3, such as 3-cyclopentyloxy-4-methoxyaniline, with arylboronic acids in the presence of a base such as triethylamine and a copper catalyst such as copper acetate (as described by Chan et al, *Tetrahedron Lett.*, 39, 2933–2936 (1998)). In general, halogenated solvents such as dichloromethane, chloroform, dichloroethane, and the like as well as nonpolar aprotic solvents such as benzene, toluene, or xylene are utilized. Such diphenylamines (e.g., 10) can more preferably be synthesized by metal catalyzed amination reactions. For example, reaction of an appropriately substituted aniline 3 with an arylhalide in the presence of a base (e.g., K$_3$PO$_4$, CSCO$_3$, or NaOtBu) and a palladium or nickel catalyst, for example Pd(dppf)Cl$_2$, a ligand (e.g., dppf) and a base (e.g., NaOtBu) (*JACS.* 1996, 118, 7217) or with Pd$_2$dba$_3$, a bulky electron rich phosphine such as P(tBu)$_3$, and a base (e.g., NaOtBu) (*J. Org. Chem.* 1999, 64, 5575) provides the desired diphenylamines 10. Solvents most commonly utilized in this type of reaction include non-polar aprotic solvents such as benzene, toluene, tetrahydrofuran, ether, and the like.

Diphenylamines 10 can then be alkylated with various alkyl halides or arylalkyl halides such as, but not limited to iodomethane, ethylbromide, benzylchloride, 3-(chloromethyl)pyridine, 4-(chloromethyl)-2,6-

Carboxylic acids 7 can be further manipulated to form carboxamides 11 using methods standard in the art. For example, a carboxylic acid can be treated with a suitable primary or secondary amine, in the presence of a suitable coupling reagent such as BOP, pyBOP or DCC, and a base such as Et$_3$N or DIEA to yield a carboxamide. These reactions generally take place in non-polar aprotic solvents such as dichloromethane, chloroform, or dichloroethane.

Carboxylic esters 6 or acids 7 can be reduced using methods standard in the art to give the corresponding carboxaldehyde or hydroxymethyl analogs. For example, an aryl ethyl ester (e.g., structure 6, R5=ethyl) can be treated with an appropriate reducing agent (e.g., LAH, DIBAL, etc.) in an aprotic solvent such as ether or THF, to produce the corresponding carboxaldehydes or hydroxymethyl analogs. Such aldehydes and alcohols can be further derivatised by methods standard in the art.

Similarly carboxamides (e.g., structure 11) and nitriles can be reduced using methods standard in the art to provide the corresponding substituted amines or aminomethyl analogs. For example, an aryl carboxamide 11 can be reduced with an appropriate reducing agent (e.g., LAH) in an aprotic solvent (e.g., benzene, toluene, ether, THF, etc.) to give the corresponding substituted aminomethyl analog. Whereas reduction of an aryl nitrile yields the corresponding primary aminomethyl analog.

SCHEME 6

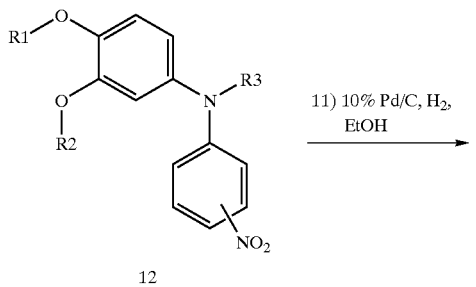
12

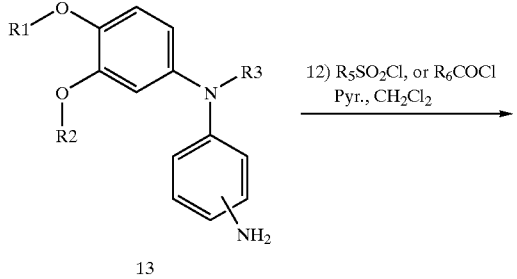
13

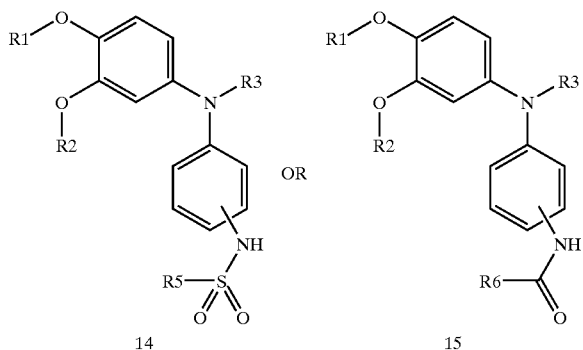
14  OR  15

Nitrobenzene compounds 12 can be reduced to the corresponding anilines 13 by methods standard in the art such as hydrogenation using a suitable catalyst (e.g., Pd on carbon) in a polar protic solvent (e.g., EtOH, MeOH, etc.). Nitrobenzenes 12 can also be reduced using a hydride source (e.g., NaBH$_4$) and a transition metal catalyst (e.g., NiCl$_2$, Pd on carbon) in polar protic solvents such as EtOH, to produce the corresponding anilines 13. These anilines can then be further substituted by methods standard in the art. For example, anilines of the type 13 can be alkylated, acylated, or sulfonylated to give the corresponding N-alkyl amines, carboxamides (e.g., structure 15) or sulfonamides (e.g., structure 14) respectively. For example, a sulfonamide can be prepared from an aniline and an appropriate sulfonyl halide or sulfonic anhydride (e.g., MeSO$_2$Cl, EtSO$_2$Cl, BnSO$_2$Cl, PhSO$_2$Cl, etc.) in the presence of a base (e.g., Et$_3$N, pyridine, DIEA, etc.). Suitable solvents for this reaction include non-polar aprotic solvents such as dichloromethane, chloroform, ether, and the like.

SCHEME 7

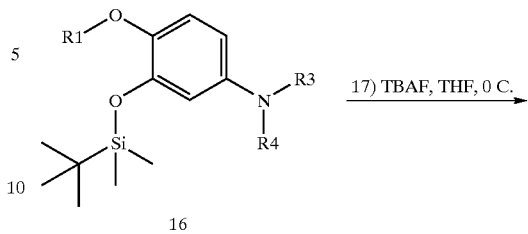
16

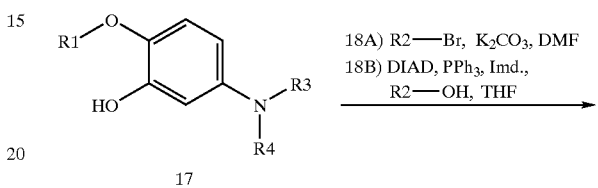
17

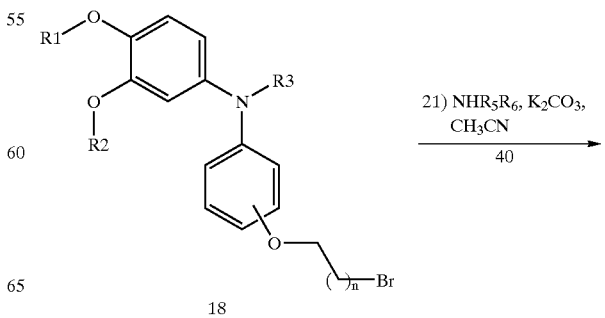
5

Trialkylsilylethers of the type 16 are prepared as described in Scheme 1. The tert-butyldimethylsilyl protected catechol intermediates 16 are readily deprotected by numerous literature methods (see Greene, T. W. and Wuts, P. G. M., Protective Groups in Organic Synthesis, 3$^{rd}$ Edition, John Wiley & Sons, 1999, pp. 273–276.) such as by using a fluoride ion source (e.g., Bu$_4$NF) in an aprotic solvent such as ether or THF; or under acidic conditions (e.g., KF, 48% HBr, DMF). The resultant phenol 17, which is a very useful synthetic intermediate, can then be alkylated by methods standard in the art and in a similar manner as described for the alkylation of nitrophenol 2 in Scheme 1. For example, by the Mitsunobu reaction, by reaction with an alkyl halide in the presence of a base, or by Ullman type aryl coupling or by reaction with vinyl-, aryl- or heteroaryl-boronic acids in the presence of a copper catalyst.

SCHEME 8

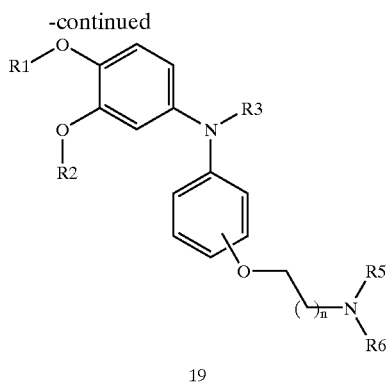

19

Haloalkoxy intermediates 18, prepared by alkylation of the corresponding phenol, can be alkylated by reactions with substituted amines, alcohols, or thiols in the presence of a base to provide analogs such as 19. For example, an alkyl halide can be aminated with an appropriate primary or secondary amine and a base such as $K_2CO_3$, in a polar aprotic solvent such as THF, DMF, or $CH_3CN$.

Many of these synthetic procedures are described more fully in the examples below.

One of ordinary skill in the art will recognize that some of the compounds of Formulae (I) and (I') can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, and substantially pure and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulae I and I' can likewise be obtained by chiral syntheses utilizing optically active starting materials.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formulae I or I' containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553–1593 (current edition).

In view of their high degree of PDE4 inhibition, the compounds of the present invention can be administered to anyone requiring or desiring PDE4 inhibition, and/or enhancement of cognition. Administration may be accomplished according to patient needs, for example, orally, nasally, parenterally (subcutaneously, intraveneously, intramuscularly, intrastemally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below its usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The present invention includes methods for dealing with memory loss separate from dementia, including mild cognitive impairment (MCI) and age-related cognitive decline. The present invention includes methods of treatment for memory impairment as a result of disease. In another application, the invention includes methods for dealing with memory loss resulting from the use of general anesthetics, chemotherapy, radiation treatment, post-surgical trauma, and therapeutic intervention.

The compounds may be used to treat psychiatric conditions including schizophrenia, bipolar or manic depression, major depression, and drug addiction and morphine dependence. These compounds may enhance wakefulness. PDE4 inhibitors can be used to raise cAMP levels and prevent neurons from undergoing apoptosis. PDE4 inhibitors are also known to be anti-inflammatory. The combination of anti-apoptotic and anti-inflammatory properties make these compounds useful to treat neurodegeneration resulting from any disease or injury, including stroke, spinal cord injury, neurogenesis, Alzheimer's disease, multiple sclerosis, amylolaterosclerosis (ALS), and multiple systems atrophy (MSA).

Thus, in accordance with a preferred embodiment, the present invention includes methods of treating patients suffering from memory impairment due to, for example, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions including acute neuronal diseases, as well as HIV and cardiovascular diseases, comprising administering an effective amount of a compound according to Formula (I) or (I') or pharmaceutically acceptable salts thereof.

The compounds of the present invention can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a further embodiment of the invention, there is provided a method of treating allergic and inflammatory disease states, comprising administering an effective amount of a compound according to Formulae (I) or (I') or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

PDE4 inhibitors for treating asthma, chronic bronchitis, psoriasis, allergic rhinitis, and other inflammatory diseases, and for inhibiting tumor necrosis factor are known within the art. See, e.g., WO 98/58901, JP11-189577, JP 10-072415, WO 93/25517, WO 94/14742, U.S. Pat. No. 5,814,651, and U.S. Pat. No. 5,935,978. These references also describ assays for determining PDE4 inhibition activity, and methods for synthesizing such compounds. The entire disclosures of these references are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, phamacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of, for example, 0.01–100 mg/kg/day, preferably 0.1–70 mg/kg/day, especially 0.5–10 mg/kg/day. Unit dosage forms can contain, for example, 0.1–50 mg of active compound. For intravenous administration, the compounds can be administered, in single or multiple dosages, at a dosage level of, for example, 0.001–50 mg/kg/day, preferably 0.001–10 mg/kg/day, especially 0.01–1 mg/kg/day. Unit dosage forms can contain, for example, 0.1–10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLE 1A

1-Cyclopentyloxy-2-methoxy-5-nitrobenzene

To a suspension of 2-methoxy-5-nitrophenol (525 g, 3.104 mol) and potassium carbonate (643.5 g, 4.66 mol) in dimethylformamide (1 L), under $N_2$ protection, was added cyclopentyl bromide (499.2 mL, 4.66 mol). The suspension was heated to 100° C. for 6 h. Potassium carbonate (85.8 g, 0.62 mol) and cyclopentyl bromide (50 mL, 0.46 mol) were added. The suspension was heated to 100° C. for 4 h. TLC indicated the reaction was complete (9:1 DCM:MeOH). The reaction mixture was cooled to room temperature and diluted with water (3L) and ether (3L). The layers were separated and the aqueous layer was re-extracted with ether (2L). The combined organic layers were washed with 1N NaOH (2L), water (2L), and brine (2L). The organic layer was dried over sodium sulfate, filtered, and evaporated. The resulting solid was azeotroped with toluene (2×300 mL) to obtain 736.7 g (99.6% yield) as a yellow solid.

The following compounds were prepared in a similar manner as described above:
  a) 1-Cyclopropylmethoxy-2-methoxy-5-nitrobenzene
  b) 1-Cyclopentoxy-2-difluoromethoxy-5-nitrobenzene
  c) 1-Cyclopropylmethoxy-2-difluoromethoxy-5-nitrobenzene

EXAMPLE 1B

2-Methoxy-5-nitro-1-((3R)-tetrahydrofuryloxy) benzene

To a mixture of 2-Methoxy-5-nitrophenol (1.69 g, 10 mmol), triphenylphosphine (5.24 g, 20 mmol) and 3-(R)-hydroxytetrahydrofuran (1.80 g, 20 mmol) in anhydrous tetrahydrofuran (40 mL) was added drop-wise, with stirring, diisopropylazodicarboxylate (4.0 mL, 20 mmol) and the mixture was allowed to stir at room temperature for 16 h. The mixture was diluted with ether (150 mL) and washed with 2N NaOH (3×50 mL) and brine (50 mL), (MgSO$_4$) and concentrated in vacuo. The crude residue was purified by flash column chromatography over silica gel (Biotage Flash 40M) eluting with 20% ethyl acetate in hexanes to give 1.05 g of product The following compounds were prepared in a similar manner as described above:
  a) 2-Methoxy-5-nitro-1-(3-tetrahydrofuryloxy)benzene
  b) 2-Methoxy-5-nitro-1-((3S)-tetrahydrofuryloxy) benzene
  c) 2-Difluoromethoxy-5-nitro-1-(3-tetrahydrofuryloxy) benzene
  d) 2-Difluoromethoxy-5-nitro-1-((3R)-tetrahydrofryloxy)benzene
  e) 2-Difluoromethoxy-5-nitro-1-((3S)-tetrahydrofuryloxy)benzene
  f) 2-Methoxy-5-nitro-1-(3-phenpropyloxy)benzene
  g) 1-(2-Indanyloxy)-4-methoxy-5-nitrobenzene

EXAMPLE 1C 1-(tert-Butyldimethylsilyl)oxy-2-methoxy-5-nitrobenzene

To a mixture of 2-methoxy-5-nitrophenol (1.53 g, 9.0 mmol) and imidazole (1.08 g, 15.9 mmol) in anhydrous DMF (40 mL) was added, with stirring, tert-butyldimethylsilyl chloride (2.05 g, 13.6 mmol) and the mixture was allowed to stir at room temperature for 16 h. The solvent was removed in vacuo and the residue was dissolved in 40 mL of 50% ethyl acetate in hexanes and filtered through 10 g of silica gel. The silica gel was washed with an additional 200 mL of 50% ethyl acetate in hexanes and the filtrates were combined and concentrated in vacuo to give 2.01 g of product as a tan crystalline solid. $^1$H NMR (CDCl$_3$) δ 7.89 (dd, 1H, J=9.0 Hz, 2.8 Hz), 7.69 (d, 1H, J=2.8 Hz), 6.88 (d, 1H, J=9.0), 3.90 (s, 3H), 1.00 (s, 9H), 0.18 (s, 6H).

EXAMPLE 2

3-Cyclopentyloxy-4-methoxyaniline

To a suspension of 10% Pd on activated carbon (25 g) in ethanol (4L), under N$_2$ protection, was added 1-cyclopentyloxy-2-methoxy-5-nitrobenzene (250 g, 1.054 mol). The reaction mixture was degassed under vacuum three times. The reaction mixture was stirred vigorously while hydrogen gas was allowed to flow over the reaction mixture. After 4 h the reaction was complete by TLC (5:1 hex:EA). The reaction mixture was filtered through a pad of celite and the celite was rinsed with additional ethanol. The solvent was removed in-vacuo to obtain 208.38 g (95% yield) of 3-cyclopentyloxy-4-methoxyaniline as a red liquid. $^1$H NMR (CDCl$_3$) δ 6.85 (d. J=8.4 Hz, 1H), 6.29 (s, 1H), 6.19 (dd, J=2.8, 8.4, 1H), 4.69 (p, J=4.4 Hz, 1H), 3.75 (s, 3H), 3.44 (bs, 2H),1.90–1.81 (m, 6H), 1.61–1.55 (m, 2H).

The following compounds were prepared in a similar manner as described above:
  a) 3-Cyclopentyloxy-4-difluoromethoxyaniline
  b) 3-Cyclopropylmethoxy-2-methoxyaniline
  c) 3-Cyclopropylmethoxy-4-difluoromethoxyaniline
  d) 4-Methoxy-3-((3R)-tetrahydrofuryloxy)aniline
  e) 4-Methoxy-3-(tetrahydrofuryloxy)aniline
  f) 4-Methoxy-3-((3S)-tetrahydrofuryloxy)aniline
  g) 4-Difluoromethoxy-3-(3-tetrahydrofuryloxy) aniline
  h) 4-Difluoromethoxy-3-((3R)-tetrahydrofuryloxy) aniline
  i) 4-Difluoromethoxy-3-((3S)-tetrahydrofuryloxy)aniline
  j) 3-(tert-Butyldimethylsilyl)oxy-4-methoxyaniline
  k) 4-Methoxy-3-(3-phenpropyloxy)aniline
  l) 3-(2-Indanyloxy)-4-methoxyaniline

EXAMPLE 3

3-Cyclopentyl-4-methoxy-N-(3-pyridyimethyl) aniline

To a mixture of 3-pyridinecarboxaldehyde (106.55 g, 0.995 mol) in methanol (5L) was added 3-cyclopentyloxy-4-methoxyaniline (208.38 g, 1.005 mol) and p-toluenesulfonic acid monohydrate (200 mg). The reaction mixture was stirred for 4 h. The flask was then cooled to 0° C. and sodium borohydride (37.64 g, 2.3 mol) was added portionwise over 4 h. The reaction mixture was allowed to warm to room temperature over 16 h with stirring. TLC indicated the reaction was complete (1:3 hex:EA). The solvent was evaporated until approximately 0.5L of slurry remained. The slurry was diluted with water (1L) and extracted with ethyl acetate (2×2L). The combined organic layers were washed with brine (500 mL), dried over sodium sulfate, and concentrated to yield 300 g (100% yield) of the desired product as a brown viscous liquid. $^1$H NMR (CDCl$_3$) δ 8.61–8.48 (m, 2H), 7.69–7.67 (m, 1H), 7.24–7.21 (m, 1H), 6.72 (d. J=8.4 Hz, 1H), 6.23 (s, 1H), 6.13 (dd, J=2.6, 8.6, 1H), 4.65 (bs, 1H), 4.27 (s, 2H), 4.0 (bs, 1H), 3.73 (s, 3H), 1.88–1.70 (m, 6H), 1.65–1.45 (m, 2H).

The following compounds were prepared in a similar manner as described above:
  a) 3-Cyclopentyloxy-4-methoxy-N-(3-thienylmethyl) aniline
  b) 3-Cyclopentyloxy-4-methoxy-N-(4-pyridylmethyl) aniline
  c) 3-Cyclopentyloxy-N-(2,6-dichloro-4-pyridylmethyl)-4-methoxyaniline
  d) 3-Cyclopentyloxy-4-methoxy-N-(2-quinolinylmethyl) aniline
  e) 3-Cyclopentyloxy-4-methoxy-N-(3-quinolinylmethyl) aniline
  f) 3-Cyclopentyloxy-4-methoxy-N-(4-quinolinylmethyl) aniline
  g) 3-Cyclopentyloxy-4-methoxy-N-(2-pyrazinylmethyl) aniline h) 4-Methoxy-N-(3-pyridylmethyl)-3-(3-tetrahydrofuryloxy)aniline
i) 4-Methoxy-N-(3-pyridylmethyl)-3-((3R)-tetrahydrofuryloxy)aniline
j) 4-Methoxy-N-(3-pyridylmethyl)-3-((3S)-tetrahydrofuryloxy)aniline
k) 3-Cyclopropylmethoxy-4-difluoromethoxy-N-(3-pyridylmethyl)aniline
l) 3-Cyclopentyloxy-4-difluoromethoxy-N-(3-pyridylmethyl)aniline
m) 4-Difluoromethoxy-N-(3-pyridylmethyl)-3-(3-tetrahydrofuryloxy)aniline
n) 4-Difluoromethoxy-N-(3-pyridylmethyl)-3-((3R)-tetrahydrofuryloxy)aniline
o) 3,4-Bis(difluoromethoxy)-N-(3-pyridylmethyl)aniline
p) 3-tert-Butyldimethylsilyloxy-4-methoxy-N-(3-pyridylmethyl)aniline
q) 3-Cyclopentyloxy-4-methoxy-N-(2-pyridylmethyl)aniline
r) 3-Cyclopentyloxy-4-methoxy-N-[1-(2-phenethyl)]aniline
s) N-Benzyl-3-cyclopentyloxy-4-methoxyaniline
t) N-[(Cyclohex-1-en-1-yl)methyl]-3-cyclopentyloxy-4-methoxyaniline
u) 3-Cyclopentyloxy-4-methoxy-N-(3,4,5-trimethoxybenzyl)aniline
v) N-[(Cyclohex-3-en-1-yl)methyl]-3-cyclopentyloxy-4-methoxyaniline
w) 3-Cyclopentyloxy-4-methoxy-N-(2,4,6-trimethylbenzyl)aniline
x) 3-Cyclopentyloxy-4-methoxy-N-(2-methylbenzyl)aniline
y) 3-Cyclopentyloxy-4-methoxy-N-(2-trifluoromethylbenzyl)aniline
z) 3-Cylclopentyloxy-4-methoxy-N-((3,4-methylenedioxy)benzyl)aniline
aa) 3-Cyclopentyloxy-N-(2-hydroxy-3-methoxylbenzyl)-4-methoxyaniline
bb) 3-Cyclopentyloxy-N-(3-furylmethyl)-4-methoxyaniline
cc) 3-Cyclopentyloxy-4-methoxy-N-(3-methylbenzyl)aniline
dd) 3-Cyclopentyloxy-4-methoxy-N-(2-methoxybenzyl)aniline
ee) 3-Cyclopentyloxy-4-methoxy-N-(3-chlorobenzyl)aniline
ff) 3-Cyclopentyloxy-4-methoxy-N-(3-methoxybenzyl)aniline
gg) 3-Cyclopentyloxy-4-methoxy-N-(2-chlorobenzyl)aniline
hh) 3-Cyclopentyloxy-4-methoxy-N-(3-methylbenzyl)aniline
ii) 4-Methoxy-3-(3-phenpropyloxy)-N-(4-pyridylmethyl)aniline
jj) N-(2,6-Dichloro-4-pyridylmethyl)-3-(2-indanyloxy)-4-methoxyaniline
kk) 4-Methoxy-3-(3-phenpropyloxy)-N-(2-pyridylmethyl)aniline
ll) N-(2,6-Dichloro-4-pyridylmethyl)-4-methoxy-3-(3-phenpropyloxy)aniline
mm) 4-Methoxy-3-(3-phenpropyloxy)-N-(3-pyridylmethyl)aniline
nn) 3-Cyclopentyloxy-4-methoxy-N-(2-thienylmethyl)aniline
oo) 3-(2-Indanyloxy)-4-methoxy-N-(3-thienylmethyl)aniline
pp) 4-Methoxy-3-(3-phenpropyloxy)-N-(3-thienylmethyl)aniline
qq) 3-(2-Indanyloxy)-4-methoxy-N-(2-pyridylmethyl)aniline
rr) 3-(2-Indanyloxy)-4-methoxy-N-(3-pyridylmethyl)aniline
ss) 3-(2-Indanyloxy)-4-methoxy-N-(4-pyridylmethyl)aniline
tt) 3-Cyclopentyloxy-4-methoxy-N-(3-piperidinemethyl)aniline
uu) 3-Cyclopentyloxy-4-methoxy-N-(3-(1-tert-butyloxycarbonyl)piperidinemethyl)aniline
vv) 3-Cyclopentyloxy-4-methoxy-N-(6-methyl-2-pyridylmethyl)aniline
ww) N-(2-Chloro-3-pyridylmethyl)-3-cyclopentyloxy-4-methoxyaniline
xx) N-(2-Chloro-5-pyridylmethyl)-3-cyclopentyloxy-4-methoxyaniline
yy) 3-Cyclopentyloxy-4-methoxy-N-(2-thiazolylmethyl)aniline

EXAMPLE 4

3-Cyclopentyloxy-4-methoxy-N-(3-pyridylmethyl)diphenylamine

To a 100 mL oven dried, argon flushed flask was added in the following order 0.59 g (6.10 mmol) of NaOtBu, 360 mg of $Pd_2dba_3$, 20 mL of toluene, 0.14 mL of $P(tBu)_3$, and a 20 mL solution of 1.3 g (4.36 mmol) of N-(3-pyridylmethyl)-3-cyclopentyloxy-4-methoxyaniline in toluene. With stirring, 3.1 g (15 mmol) of iodobenzene was added dropwise and the mixture was stirred for 18 hours. The reaction mixture was diluted with EtOAc and washed twice with $H_2O$ and extracted with 3×15 mL of 3N HCl. The combined acid extracts were washed with 15 mL of EtOAc and then carefully neutralized with 6N NaOH to pH greater than 12. The basic solution was extracted with 2×15 mL of EtOAc and the combined organic fractions were subsequently washed with 15 mL of $H_2O$ and brine, dried ($MgSO_4$), and concentrated. The residue was purified by chromatography over silica gel (Biotage Flash 40M) eluting with 25% EtOAc in hexanes. The material was further purified by crystallization from hexanes to give 550 mg of a white solid. $^1H$ NMR ($CDCl_3$) δ 8.61 (s, 1H), 8.49 (d, 1H, J=4.2 Hz), 7.67 (d, 1H, 7.9 Hz), 7.30–7.10 (m, 3H), 6.90–6.80 (m, 4H), 6.80–6.60 (m, 2H), 4.94 (s, 2H), 4.64 (p, 1H, J =4.1 Hz),3.84 (s, 3H), 1.86–1.70 (m, 6H), 1.65–1.45 (m, 2H).

The following compounds were prepared in a similar manner as described above:
a) 3-Cyclopentyloxy-4-methoxy-2'-methyl-N-(3-pyridylnethyl)diphenylamine
b) 3-Cyclopentyloxy-4-methoxy-3'-methyl-N-(3-pyridylmethyl)diphenylamine
c) 3-Cyclopentyloxy-4-methoxy-4'-methyl-N-(3-pyridylmethyl)diphenylamine
d) 3-Cyclopentyloxy-4'-ethyl-4-methoxy-N-(3-pyridylmethyl)diphenylamine
e) 3'-Chloro-3-cyclopentyloxy-4-methoxy-N-(3-pyridylmethyl)diphenylamine
f) 4'-Chloro-3-cyclopentyloxy-4-methoxy-N-(3-pyridylmethyl)diphenylamine g) 3-Cyclopentyloxy-2',4-dimethoxy-N-(3-pyridylmethyl)diphenylamine h) 3-Cyclopentyloxy-3',4-dimethoxy-N-(3-pyridylmethyl)diphenylamine i) 3-Cyclopentyloxy-4,4'-dimethoxy-N-(3-pyridylmethyl)diphenylamine j) 3-Cyclopentyloxy-4-methoxy-N-(3-pyridylmethyl)-3'-trifluoromethyldiphenylamine k) 3-Cyclopentyloxy-4-methoxy-N-(3-pyridylmethyl)-4'-trifluoromethyldiphenylamine l) 3-Cyclopentyloxy-3'-fluoro-4-methoxy-N-(3-pyridylmethyl)diphenylamine m) 3-Cyclopentyloxy-4'-fluoro-4-methoxy-N-(3-pyridylmethyl)diphenylamine n) 3-Cyclopentyloxy-4-methoxy-3'-phenyl-N-(3-pyridylmethyl)diphenylamine o) 3-Cyclopentyloxy-4-methoxy-4'-phenyl-N-(3-pyridylmethyl)diphenylamine p) 3'-Cyano-3-cyclopentyloxy-4-methoxy-N-(3-pyridylmethyl)diphenylamine q) 4'-Cyano-3-cyclopentyloxy-4-methoxy-N-(3-pyridylmethyl)diphenylamine r) Ethyl N-(3-cyclopentyloxy-4-methoxypenyl)-N-(3-pyridylmethyl)-3-aminobenzoate s) Ethyl N-(3-cyclopentyloxy-4-methoxyphenyl)-N-(3-pyridylmethyl)-4-aminobenzoate t) 3-Cyclopentyloxy-4-methoxy-3'-nitro-N-(3-pyridylmethyl)diphenylamine u) 3-Cyclopentyloxy-4-methoxy-4'-nitro-N-(3-pyridylmethyl)diphenylamine v) N-(3-Cyclopentyloxy-4-methoxyphenyl)-N-(3-pyridylmethyl)-1-naphthylamine w) 3-Cyclopentyloxy-2',3'-dimethyl-4-methoxy-N-(3-pyridylmethyl)diphenylamine x) 3-Cyclopentyloxy-2',4'-dimethyl-4-methoxy-N-(3-pyridylmethyl)diphenylamine y) 3-Cyclopentyloxy-2',5'-dimethyl-4-methoxy-N-(3-pyridylmethyl)diphenylamine z) 3-Cyclopentyloxy-3',4'-dimethyl-4-methoxy-N-(3-pyridylmethyl)diphenylamine aa) 3-Cyclopentyloxy-2',3'-dichloro-4-methoxy-N-(3-pyridylmethyl)diphenylamine bb) 3-Cyclopentyloxy-3',3,4'-dichloro-4-methoxy-N-(3-pyridylmethyl)diphenylamine cc) 3-Cyclopentyloxy-3',5'-dichloro-4-methoxy-N-(3-pyridylnethyl)diphenylamine dd) 3'-Chloro-3-cyclopentyloxy-4'-fluoro-4-methoxy-N-(3-pyridylmethyl)diphenylamine ee) 4'-Chloro-3-cyclopentyloxy-3'-fluoro-4-methoxy-N-(3-pyridylmethyl)diphenylamine ff) 4'-Chloro-3-cyclopentyloxy-4-methoxy-N-(3-pyridylmethyl)-3'-trifluoromethyldiphenylamine gg) 3-Cyclopentyloxy-4-methoxy-N-(3-thienylmethyl)diphenylamine hh) N-(3-Cyclopentyloxy-4-methoxyphenyl)-N-(3-thienylmethyl)-1-naphthylamine ii) 3-Cyclopentyloxy-2',3'-dichloro-4-methoxy-N-(3-thienylnethyl)diphenylamine jj) 3-Cyclopentyloxy-4-methoxy-4'-methyl-N-(4-pyridylmethyl)diphenylamine kk) 3-Cyclopentyloxy-N-(2,6-dichloro-4-pyridylmethyl)-4-methoxy-3'-methyldiphenylamine ll) 2'-Chloro-3-cyclopentyloxy-N-(2,6-dichloro-4-pyridylmethyl)-4-methoxydiphenylamine mm) 3-Cyclopentyloxy-N-(2,6-dichloro-4-pyridylmethyl)-4-methoxydiphenylamine nn) 3-Cyclopentyloxy-4-methoxy-N-(6-methyl-2-pyridylmethyl)diphenylamine oo) 3-Cyclopentyloxy-4-methoxy-N-(3-quinolinylmethyl)diphenylamine pp) 3-Cyclopentyloxy-4-methoxy-N-(4-quinolinylmethyl)diphenylamine qq) 3-Cyclopentyloxy-4-methoxy-N-(2-pyrazinylmethyl)diphenylamine rr) 4-Methoxy-3'-methyl-N-(3-pyridylmethyl)-3-(3-tetrahydrofuryloxy)diphenylamine ss) 4-Methoxy-4'-methyl-N-(3-pyridylmethyl)-3-(3-tetrahydrofuryloxy)diphenylamine tt) 4,4'-Dimethoxy-N-(3-pyridylmethyl)-3-(3-tetrahydrofuryloxy)diphenylamine uu) 3'-Chloro-4-methoxy-N-(3-pyridylmethyl)-3-(3-tetrahydrofuryloxy)diphenylamine vv) 4-Methoxy-4'-(4-methylpiperazin-1-ylcarbonyl)-N-(3-pyridylmethyl)-3-(3-tetrahydrofuryloxy) diphenylamine ww) 3'-Cyano-4-methoxy-N-(3-pyridylmethyl)-3-((3R)-tetrahydrofuryloxy)diphenylamine xx) 3'-Cyano-4-methoxy-N-(3-pyridylmethyl)-3-((3R)-tetrahydrofuryloxy)diphenylamine yy) 3-Cyclopropylmethoxy-4-difluoromethoxy-N-(3-pyridylmethyl)diphenylamine zz) 3-Cyclopentyloxy-4-difluoromethoxy-N-(3-pyridylmethyl)diphenylamine aaa) 4-Difluoromethoxy-N-(3-pyridylmethyl)-3-(3-tetrahydrofuryloxy)diphenylamine bbb) 3,4-Bis(difluoromethoxy)-N-(3-pyridylmethyl)diphenylamine ccc) 4-Difluoromethoxy-N-(3-pyridylmethyl)-3-((3R)-tetrahydrofuryloxy)diphenylamine ddd) 3'-Cyano-4-difluoromethoxy-N-(3-pyridylnethyl)-3-((3R)-tetrahydrofuryloxy)diphenylamine eee) 3'-Chloro-4-difluoromethoxy-N-(3-pyridylmethyl)-3-((3R)-tetrahydrofuryloxy)diphenylamine fff) Ethyl N-(3-cyclopropylmethoxy-4-difluoromethoxyphenyl)-N-(3-pyridylmethyl)-3-aminobenzoate ggg) 3-Cyclopentyloxy-4-methoxy-3'-(4-methylpiperazin-1-ylcarbonyl)-N-(3-pyridylmethyl)diphenylamine hhh) 3-Cyclopentyloxy-4-methoxy-4'-(4-methylpiperazin-1-ylcarbonyl)-N-(3-pyridylmethyl)diphenylamine iii) 3'-tert-Butyldimethylsilyloxy-3-cyclopentyloxy-4-methoxy-N-(3-pyridylmethyl)diphenylamine jjj) 4'-tert-Butyldimethylsilyloxy-3-cyclopentyloxy-4-methoxy-N-(3-pyridylmethyl)diphenylamine kkk) tert-Butyl N-(3-cyclopentyloxy-4-methoxyphenyl)-N-(3-pyridylmethyl)-3-aminobenzoate lll) Ethyl N-(3-cyclopentyloxy-4-difluoromethoxyphenyl)-N-(3-pyridylmethyl)-3-aminobenzoate mmm) Ethyl N-(4-difluoromethoxy-3-(3-tetrahydrofuryloxy)phenyl)-N-(3-pyridylmethyl)-3-aminobenzoate nnn) Ethyl N-(3,4-Bis(difluoromethoxy)phenyl)-N-(3-pyridylmethyl)-3-aminobenzoate ooo) Ethyl N-(4-methoxy-3-((3R)-tetrahydrofuryloxy)phenyl)-N-(3-pyridylmethyl)-3-aminobenzoate ppp) Ethyl N-(3-cyclopropylmethoxy-4-methoxyphenyl)-N-(3-pyridylmethyl)-3-aminobenzoate qqq) 3-Cyclopentyloxy-4-methoxy-4'-(2-(tetrahydropyran-2-yl)-2H-tetrazol-5-yl)-N-(3-pyridylmethyl)diphenylamine rrr) 3-Cyclopentyloxy-4-methoxy-3'-(2-(tetrahydropyran-2-yl)-2H-tetrazol-5-yl)-N-(3-pyridylmethyl)diphenylamine sss) 4-Methoxy-4'-(2-(tetrahydropyran-2-yl)-2H-tetrazol-5-yl)-N-(3-pyridylmethyl)-3-((3R)-tetrahydrofuryloxy)diphenylamine ttt) 3-Cyclopropylmethoxy-4-methoxy-4'-(2-(tetrahydropyran-2-yl)-2H-tetrazol-5-yl)-N-(3 pyridylmethyl)diphenylamine uuu) 4-Difluoromethoxy-4'-(2-(tetrahydropyran-2-yl)-2H-tetrazol-5-yl)-N-(3-pyridylmethyl)-3-((3R)-tetrahydrofuryloxy)diphenylamine vvv) 3-Cyclopropylmethoxy-4-difluoromethoxy-4'-(2-(tetrahydropyran-2-yl)-2H-tetrazol-5-yl)-N-(3-pyridylmethyl)diphenylamine www) 3-Cyclopentyloxy-4-difluoromethoxy-4'-(2-(tetrahydropyran-2-yl)-2H-tetrazol-5-yl-N-(3-pyridylmethyl)diphenylamine xxx) 3-Cyclopropylmethoxy-4-difluoromethoxy-3'-(2-(tetrahydropyran-2-yl)-2H-tetrazol-5-yl)-N-(3-pyridylmethyl)diphenylamine yyy) Bis-(3,4-difluoromethoxy)-3'-(2-(tetrahydropyran-2-yl)-2H-tetrazol-5-yl)-N-(3-pyridylmethyl)diphenylamine zzz) 3-tert-Butyldimethylsilyloxy-4-methoxy-N-(3-pyridylmethyl)diphenylamine aaaa) 3-tert-Butyldimethylsilyloxy-3'-chloro-4-methoxy-N-(3-pyridylmethyl)diphenylamine bbbb) Ethyl N-(3-tert-butyldimethylsilyloxy-4-methoxyphenyl)-N-(3-pyridylmethyl)-3-aminobenzoate cccc) 3-Cyclopentyloxy-2'-chloro-4-methoxy-N-(3-pyridylmethyl)diphenylamine dddd) 3-(2-indanyloxy)-4-methoxy-N-(3-pyridylmethyl)diphenylamine

EXAMPLE 5

N-(3-Cyclopentyloxy-4-methoxyphenyl)-N-(3-pyridylmethyl)-3-aminobenzoic acid

A solution of 6.5 g of ethyl N-(3-cyclopentyloxy-4-methoxyphenyl)-N-(3-pyridylmethyl)-3-aminobenzoate in 50 mL of EtOH was treated with 10 mL of 6N NaOH. The mixture was allowed to stand for 6 hours, concentrated, and diluted with 50 mL of $H_2O$. The aqueous mixture was extracted with 2×50 mL of ether, acidified with AcOH to pH 3, and extracted with 2×50 mL of EtOAc. The combined EtOAc fractions were washed with 25 mL of $H_2O$ and 25 mL of brine, dried ($MgSO_4$), and concentrated. The residue was purified by chromatography over $SiO_2$ (35 g RediSep® column) using a linear gradient of EtOAc and hexanes as eluant (50% EtOAc to 70% EtOAc over 20 minutes) to provide 4.8 g of a yellow solid product after drying in vacuo for 12 h at 60° C. $^1$H NMR ($CDCl_3$) δ 11.15 (bs, 1H), 8.70–8.55 (m, 2H), 7.77–6.71 (m, 9H), 4.99 (s, 2H), 4.65 (p, J=3.8 Hz, 1H), 3.84 (s, 3H), 1.86–1.70 (m, 6H), 1.65–1.45 (m, 2H).

The following compounds were prepared in a similar manner as described above:

a) N-(3-Cyclopentyloxy-4-methoxyphenyl)-N-(3-pyridylmethyl)-4-aminobenzoic acid b) N-(3-Cyclopentyloxy-4-difluoromethoxyphenyl)-N-(3-pyridylmethyl)-3-aminobenzoic acid c) N-[4-Difluoromethoxy-3-(3-tetrahydrofuryloxy)phenyl]-N-(3-pyridylmethyl)-3-aminobenzoic acid d) N-3,4-Bis(difluoromethoxy)phenyl)-N-(3-pyridylmethyl)-3-aminobenzoic acid e) N-[4-Methoxy-3-((3R)-tetrahydrofuryloxy)phenyl]-N-(3-pyridylmethyl)-3-aminobenzoic acid f) N-(3-Cyclopropylmethoxy-4-methoxyphenyl)-N-(3-pyridylmethyl)-4-aminobenzoic acid g) N-(3-Cyclopropylmethoxy-4-difluoromethoxyphenyl)-N-(3-pyridylmethyl)-3-aminobenzoic acid h) N-(3-Cyclopentyloxy-4-methoxyphenyl)-3-aminobenzoic acid i) N-[3-(4-Chlorophenyl)prop-1-yloxy-4-methoxyphenyl]-N-(3-pyridylmethyl)-3-aminobenzoic acid j) N-(3-Cyclopropylmethoxy-4-methoxyphenyl)-N-(3-pyridylmethyl)-3-aminobenzoic acid k) N-[3-(2-Indanyloxy)-4-methoxyphenyl]-N-(3-pyridylmethyl)-3-aminobenzoic acid l) N-[4-Methoxy-3-(3-tetrahydrofuryloxy)phenyl]-N-(3-pyridylmethyl)-3-aminobenzoic acid m) N-[4-Methoxy-3-((3R)-tetrahydrofuryloxy)phenyl]-N-(3-pyridylmethyl)-3-aminobenzoic acid n) N-[3-(2-Methoxyethoxy)-4-methoxyphenyl]-N-(3-pyridylmethyl)-3-aminobenzoic acid o) N-[4-Methoxy-3-(2-(2-pyridyl)ethyl)oxyphenyl]-N-(3-pyridylmethyl)-3-aminobenzoic acid

EXAMPLE 6

N-(3-Cyclopentyloxy-4-methoxyphenyl)-N-(3-pyridylmethyl)-2-aminobenzoic acid

Tert-Butyl N-(3-cyclopentyloxy-4-methoxyphenyl)-N-(3-pyridylmethyl)-2-aminobenzoate (60 mg, 0.13 mmol) was taken up in 2 mL 98% formic acid and heated at 40° C. for 4 h. The formic acid was removed in vacuo and the residue was loaded onto a column of silica gel (RediSep, 4.2 g). The product was eluted with a linear gradient from 40% EtOAc in hexanes to 60% EtOAc in hexanes over 15 min to yield 16 mg of product as a brown solid. $^1$H NMR ($CDCl_3$) δ8.47 (d, 1H, J=4.9), 8.43 (s, 1H), 8.10 (d, 1H, J=7.8), 7.67 (d, 1H, J=7.8 Hz), 7.56 (m, 1H), 7.40–7.20 (m, 3H), 6.75 (d, 1H, J=8.7), 6.57 (d, 1H, J=8.7), 6.47 (s, 1H), 4.72 (s, 2H), 4.54 (p, 1H, J=4.3), 3.77 (s, 3H), 1.80–1.60 (m, 6H), 1.60–1.40 (m, 2H).

The following compounds were prepared in a similar manner as described above:

a) N-(3-Cyclopentyloxy-4-methoxyphenyl)-N-(3-pyridylmethyl)-3-aminobenzoic acid b) N-(3-Cyclopentyloxy-4-methoxyphenyl)-N-(3-pyridylmethyl)-6-aminonicotinic acid

EXAMPLE 7

3-Cyclopropylmethyloxy-4-difluoromethoxy-N-(3-pyridylmethyl)-4'-(2H-tetrazol-5-yl)diphenylamine 3-Cyclopropylmethoxy-4-difluoromethoxy-N-(3-pyridylmethyl)-4'-[2-(2-tetrahydropyranyl)-2H-tetrazol-5- yl]diphenylamine (1.5 g, 0.26 mmol) was dissolved in THF (5 mL) and 3 mL of 1N HCl was added. After 6 h at room temperature, the mixture was neutralized to pH=5 with saturated aqueous sodium bicarbonate and extracted with EtOAc (3×50 mL). The EtOAc extracts were combined, washed with brine (50 mL), dried (MgSO$_4$), and concentrated in vacuo. The crude residue was loaded onto a RediSep column (10 g, silica gel) and the product was eluted using a linear gradient from 0% MeOH in EtOAc to 5% MeOH in EtOAc over 20 min to give 0.96 g of product as a white powder. $^1$H NMR (CD$_3$OD) δ8.55 (s, 1H), 8.43 (d, 1H, J=4.9 Hz), 7.65 (d, 1H, 8.0 Hz), 7.21 (dd, 1H, J=4.9 Hz, 8.0 Hz), 7.18 (d, 1H, J=8.9 Hz), 7.10–6.90 (m, 3H), 6.87 (dd, 1H, J=8.6 Hz, 2.5 Hz), 6.75 (t, 1H, J=75.5 Hz), 5.14 (s, 2H), 3.82 (d, 2H, J=6.9 Hz), 1.23 (m, 1H), 0.60 (m, 2H), 0.33 (m, 2H).

The following compounds were prepared in a similar manner as described above:

a) 3-Cyclopentyloxy-4-methoxy-N-(3-pyridylmethyl)-4'-(2H-tetrazol-5-yl)diphenylamine
b) 3-Cyclopentyloxy-4-methoxy-N-(3-pyridylmethyl)-3'-(2H-tetrazol-5-yl)diphenylamine
c) 4-Methoxy-N-(3-pyridylmethyl)-3-((3R)-tetrahydrofuryloxy)-4'-(2H-tetrazol-5-yl)diphenylamine
d) 3-Cyclopropylmethyloxy-4-methoxy-N-(3-pyridylmethyl)-4'-(2H-tetrazol-5-yl)diphenylamine
e) 4-Difluoromethoxy-N-(3-pyridylmethyl)-3-((3R)-tetrahydrofuryloxy)-4'-(2H-tetrazol-5-yl)diphenylamine
f) 3-Cyclopentyloxy-4-difluromethoxy-N-(3-pyridylmethyl)-4'-(2H-tetrazol-5-yl)diphenylamine
g) 3-Cyclopropylmethyloxy-4-difluoromethoxy-N-(3-pyridylmethyl)-3'-(2H-tetrazol-5-yl)diphenylamine
h) Bis-3,4-difluoromethoxy-N-(3-pyridylmethyl)-4'-(2H-tetrazol-5-yl)diphenylamine

EXAMPLE 8 (Method A)

3-Cyclopentyloxy-4-methoxydiphenylamine

Method A. (Ref. Chan, D. M. T.; Monaco, K. L.; Wang, R. P.; Winters, M. P., *Tetrahedron Lett.*, 1998, 39, 2933–2936.). A slurry of 207 mg of 4-methoxy-3-cyclopentyloxyaniline, 280 mg of phenylboronic acid, 182 mg of Cu(OAc)$_2$, 280 μL of Et$_3$N and 4.0 mL of CH$_2$Cl$_2$ was stirred for 20 h at room temp. The black mixture was filtered through silica eluting with CH$_2$Cl$_2$, concentrated, and purified by chromatoghraphy over SiO$_2$ using EtOAc/Hexanes (15/85) as eluant to provide 75 mg of the desired product. $^1$H NMR (CDCl$_3$) δ7.26–7.20 (m, 2H), 6.94–6.63 (m, 6H), 5.50 (s, 1H), 4.71 (m, 1H), 3.82 (s, 3H), 1.89–1.54 (m, 8H).

The following compounds were prepared in a similar manner as described above:

a) 3-Cyclopentyloxy-3',4-dimethoxydiphenylamine
b) 3'-Chloro-3-cyclopentyloxy-4-methoxydiphenylamine
c) 3-Cyclopentyloxy-4-methoxy-3'methyldiphenylamine
d) 3-Cyclopentyloxy-4'-fluoro-4-methoxydiphenylamine
e) 3-Cyclopentyloxy-4-methoxy-4'-vinyldiphenylamine
f) 3'-Cyano-3-cyclopentyloxy-4-methoxydiphenylamine
g) 4'-Chloro-3-cyclopentyloxy-4-methoxydiphenylamine
h) 3-Cyclopentyloxy-4,4'-dimethoxydiphenylamine
i) 3-Cyclopentyloxy-4-methoxy-2'-methyldiphenylamine
j) 3-Cyclopentyloxy-4-methoxy-4-methyldiphenylamine
k) 2'-Chloro-3-cyclopentyloxy-4-methoxydiphenylamine
l) 3-Cyclopentyloxy-2',4-dimethoxydiphenylamine
m) 3-Cyclopentyloxy-4-methoxy-3'-trifluoromethyldiphenylamine
n) 3-Cyclopentyloxy-4-methoxy-4'-trifluoromethyldiphenylamine
o) 3-Cyclopentyloxy-2',5'-dimethyl-4-methoxydiphenylamine

EXAMPLE 8 (Method B)

3-Cyclopentyloxy-4-methoxydiphenylamine

Method B (*Angerw Chem. Int. Ed.,* 1995, 34(17), 1348–1351.) A mixture of 207 mg of 3-cyclopentyloxy-4-methoxyaniline, 204 mg of iodobenzene, 115 mg of NaOtBu, 9 mg of Pd$_2$(dba)$_3$, 12 mg of P(o-tol)$_3$ and 7 mL of toluene was combined and warmed with stirring to 100° C. for 4 h. The mixture was cooled to room temp, diluted with 25 mL of EtOAc and washed with 10 mL of H$_2$O, 10 mL of brine, dried (MgSO$_4$) and concentrated. The residue was purified by chromatography over SiO$_2$ using EtOAc/hexanes (5/95) as eluant to provide 84 mg of the desired product.

The following compounds were prepared in a similar manner as described above:

a) 3-Cyclopentyloxy-4-methoxy-2',4'-dimethyldiphenylamine
b) 3-Cyclopentyloxy-2',5'-dimethyl-4-methoxydiphenylamine
c) 3-Cyclopentyloxy-2',3'-dimethyl-4-methoxydiphenylamine
d) 3-Cyclopentyloxy-3',4'-dimethyl-4-methoxydiphenylamine
e) 3-Cyclopentyloxy-3',4'-methylenedioxydiphenylamine
f) 4'-tert-Butyl-3-cyclopentyloxy-4-methoxydiphenylamine
g) 3-Cyclopentyloxy-3',4'-dichloro-4-methoxydiphenylamine
h) 3-Cyclopentyloxy-2',3'-dichloro-4-methoxydiphenylamine

EXAMPLE 8 (Method C)

3-Cyclopentyloxy-2',4,5'-trimethoxydiphenylamine

Method C. To a mixture of Pd(dppf)Cl$_2$ (0.025 mmol, 5 mol %), dppf (0.075 mmol, 3 dppf/Pd) and NaOtBu (0.70 mmol, 1.4 equivalents) and 1.0 mL THF was added 1-bromo-2,5-dimethoxybenzene (0.55 mmol, 1.1 equivalents) followed by 1.0 mL of a 0.5M solution of 3-cyclopentyloxy-4-methoxyaniline in THF. The mixture was heated to 60° C. for 3 hours and diluted with ether and washed with H$_2$O and brine, dried (MgSO$_4$), and concentrated. The crude residue was purified by chromatography over silica gel (Biotage Flash 12) eluting with 15% EtOAc in hexanes.

The following compounds were prepared in a similar manner as described above:

a) N-(3-Cyclopentyloxy-4-methoxyphenyl)-3-pyridylamine
b) 3-Cyclopentyloxy-2',4',4-trimethoxydiphenylamine
c) N-(3-Cyclopentyloxy-4-methoxyphenyl)-2-pyridylamine
d) N-(3-Cyclopentyloxy-4-methoxyphenyl)-8-quinolinylamine e) N-(3-Cyclopentyloxy-4-methoxyphenyl)-2-naphthylamine
f) N-(3-Cyclopentyloxy-4-methoxyphenyl)-1-naphthylamine
g) 3-Cyclopentyloxy-4'-ethyl-4-methoxydiphenylamine
h) 3-Cyclopentyloxy-2'-fluoro-4-methoxy-5'-methyldiphenylamine
i) 3-Cyclopentyloxy-3'-fluoro-4-methoxy-4'-methyldiphenylamine
j) N-(3-Cyclopentyloxy-4-methoxyphenyl)-2-pyrimidinylamine
k) 3-Cyclopentyloxy-3',5'-dichloro-4-methoxydiphenylamine
l) 3-Cyclopentyloxy-2'-ethyl-4-methoxydiphenylamine
m) 4'-Chloro-3-cyclopentyloxy-3'-fluoro-4-methoxydiphenylamine
n) N-(3-Cyclopentyloxy-4-methoxyphenyl)-4-isoquinolinylamine
o) N-(3-Cyclopentyloxy-4-methoxyphenyl)-2-pyrazinylamine
p) N-(3-Cyclopentyloxy-4-methoxyphenyl)-5-pyrimidinylamine
q) N-(3-Cyclopentyloxy-4-methoxyphenyl)-1-isoquinolinylamine
r) N-(3-Cyclopentyloxy-4-methoxyphenyl)-3-quinolinylamine
s) N-(3-Cyclopentyloxy-4-methoxyphenyl)-4-pyridylamine
t) N-(3-Cyclopentyloxy-4-difluoromethoxyphenyl)-3-pyridylamine
u) N-(3-Cyclopropylmethyloxy-4-methoxyphenyl)-3-pyridylamine
v) N-(3-Cyclopropylmethyloxy-4-difluoromethoxyphenyl)-3-pyridylamine
w) N-(4-Methoxy-3-(3R)-tetrahydrofuryloxyphenyl)-3-pyridylamine
x) N-(4-Difluoromethoxy-3-(3R)-tetrahydrofuryloxyphenyl)-3-pyridylamine
y) Ethyl N-(3-cyclopentyloxy-4-methoxyphenyl)-3-aminobenzoate
z) 3-Cyclopentyloxy-4'-(N,N-dimethylamino)-4-methoxydiphenylamine
aa) N-(3-Cyclopentyloxy-4-methoxyphenyl)-3-(6-methoxypyridyl)amine
bb) Methyl N-(3-cyclopentyloxy-4-methoxyphenyl)-2-aminonicotinate
cc) tert-Butyl N-(3-cyclopentyloxy-4-methoxyphenyl)-6-aminonicotinate
dd) 2'-Amino-3-cyclopentyloxy-4-methoxydiphenylamine
ee) 3-Cyclopentyloxy-4-methoxy-3'-(1-phthalimido)diphenylamine
ff) 3-Cyclopentyloxy-4-methoxy-3'-[2-(2-tetrahydropyranyl)-2H-tetrazol-5-yl]diphenylamine EXAMPLE 9 (Method A)

3-Cyclopentyloxy-4-methoxy-N-methyldiphenylamine

To a solution of 3-cyclopentyloxy-4-methoxydiphenylamine (70 mg, 0.25 mmol) in 3 mL of THF at 0° C. was added 0.55 mL of 0.5 M KN(TMS)$_2$ in toluene. The solution was stirred at 0° C. for 0.5 h and 2.0 equivalents of iodomethane was added and the reaction mixture was warmed to room temperature. Upon reaction completion as indicated by TLC, 10 mL of EtOAc was added and the mixture was washed with 3 mL of H$_2$O, 3 mL of brine, dried (MgSO$_4$) and concentrated. The crude residue was purified by column chromatography (Biotage flash 12) using 5% EtOAc in hexanes as eluant.

The following compounds were prepared in a similar manner as described above:

a) 3-Cyclopentyloxy-N-ethyl-4-methoxydiphenylamine
b) 3-Cyclopentyloxy-4-methoxy-N-(1-propyl)diphenylamine
c) 3-Cyclopentyloxy-4-methoxy-N-[1-(3-phenpropyl)]diphenylarnine
d) N-Benzyl-3-cyclopentyloxy-4-methoxydiphenylamine
e) 3-Cyclopentyloxy-4-methoxy-N-(4-pyridylmethyl)diphenylamine
f) 3-Cyclopentyloxy-4-methoxy-N-(2-pyridylmethyl)diphenylamine
g) 3-Cyclopentyloxy-4-methoxy-N-(3-pyridylmethyl)diphenylamine
h) 3-Cyclopentyloxy-4-methoxy-N-[3-(3-pyridyl)-1-propyl]diphenylamine
i) N-(3-Cyclopentyloxy-4-methoxyphenyl)-N-ethyl-4-isoquinolinylamine
j) N-(3-Cyclopentyloxy-4-methoxyphenyl)-N-benzyl-4-isoquinolinylamine
k) N-(3-Cyclopentyloxy-4-methoxyphenyl)-N-methyl-4-isoquinolinylamine
l) N-(3-Cyclopentyloxy-4-methoxyphenyl)-N-propyl-4-isoquinolinylamine
m) N-(3-Cyclopentyloxy-4-methoxyphenyl)-N-(4-isoquinolinyl)-N-(4-pyridylmethyl)amine
n) N-(3-Cyclopentyloxy-4-methoxyphenyl)-N-(4-isoquinolinyl)-N-(3-pyridylmethyl)amine
o) N-(3-Cyclopentyloxy-4-methoxyphenyl)-N-(3-pyridylmethyl)-N-(5-pyrimidinyl)amine
p) N-(3-Cyclopentyloxy-4-methoxyphenyl)-N-(2-pyrazinyl)-N-(3-pyridylmethyl)amine
q) N-(3-Cyclopentyloxy-4-methoxyphenyl)-N-(2-pyridyl)-N-(3-pyridylmethyl)amine
r) N-(3-Cyclopentyloxy-4-methoxyphenyl)-N-(3-pyridyl)-N-(3-pyridylmethyl)amine
s) N-(3-Cyclopentyloxy-4-methoxyphenyl)-N-(4-pyridyl)-N-(3-pyridylmethyl)amine
t) tert-Butyl N-(3-cyclopentyloxy-4-methoxyphenyl)-N-(3-pyridylmethyl)-6-aminonicotinate
u) N-(3-Cyclopropylmethoxy-4-methoxyphenyl)-N-(3-pyridyl)-N-(3-pyridylmethyl)amine
v) N-(4-Methoxy-3-(3R)-tetrahydrofuryloxyphenyl)-N-(3-pyridyl)-N-(3-pyridylmethyl)amine
w) N-(3-Cyclopentyloxy-4-difluoromethoxyphenyl)-N-(3-pyridyl)-N-(3-pyridylmethyl)amine
x) N-(3-Cyclopropylmethoxy-4-difluoromethoxyphenyl)-N-(3-pyridyl)-N-(3-pyridylmethyl)amine
y) N-(4-Difluoromethoxy-3-(3R)-tetrahydrofuryloxyphenyl)-N-(3-pyridyl)-N-(3-pyridylmethyl)amine
z) N-(4-Chloro-3-pyridylmethyl)-N-(3-cyclopentyloxy-4-methoxyphenyl)-N-(2-pyridyl)amine
aa) N-(3-cyclopentyloxy-4-methoxyphenyl)-N-(4-methyl-3-pyridylmethyl)-N-(2-pyridyl)amine bb) 3-Cyclopentyloxy-4-methoxy-N-(2-thiazolylmethyl) diphenylamine
cc) N-(2-Chloro-3-pyridylmethyl)-3-cyclopentyloxy-4-methoxydiphenylamine
dd) N-(6-Chloro-3-pyridylmethyl)-3-cyclopentyloxy-4-methoxydiphenylamine

EXAMPLE 9 (Method B)

N-4-Chloro-3-pyridylmethyl)-N-(3-cyclopentyl-4-methoxyphenyl)-N-(2-pyridyl)amine To a solution of (3-cyclopentyloxy-4-methoxyphenyl)-2-pyridylamine (30 mg, 0.10 mmol) and 4-chloropicolyl chloride hydrochloride (50 mg, 0.25 mmol) was dissolved in DMF (1 mL) and sodium hydride (50 mg of a 60% mineral oil dispersion, 1.3 mmol) was added in small portions. After stirring for 1 h at room temperature, the mixture was poured into 25 mL ice water. The mixture was extracted with EtOAc (2×15 mL) and the EtOAc extracts were combined, washed with brine (15 mL), dried (MgSO$_4$), and concentrated in vacuo. The crude residue was loaded onto a RediSep column (4.2 g, silica gel) and the product was eluted with 15% EtOAc in hexanes to give 20 mg of product as a yellow crystalline solid. $^1$H NMR (CDCl$_3$) δ8.61 (s, 1H), 8.34 (d, 1H, J=5.3 Hz), 8.17 (d, 1H, 5.0 Hz), 7.33 (m, 1H), 7.25 (m, 1H), 6.83 (d, 1H, J=8.5), 6.75 (d, 1H, J=8.5), 6.71 (s, 1H), 6.62 (m, 1H), 6.42 (d, 1H, J=8.6), 5.32 (s, 2H), 4.63 (p, 1H, J=4.12 Hz), 3.83 (s, 3H), 1.86–1.70 (m, 6H), 1.65–1.45 (m, 2H).

The following compounds were prepared in a similar manner as described above:

a) 3,4-Bis(difluoromethoxy)-N-(4-chloro-3-pyridylmethyl)-3'-(2-(tetrahydropyran-2-yl)-2H-tetrazol-5-yl)diphenylamine
b) 3,4-Bis(difluoromethoxy)-N-(4-methyl-3-pyridylmethyl)-3'-(2-(tetrahydropyran-2-yl)-2H-tetrazol-5-yl)diphenylamine

EXAMPLE 10

3-Cyclopentyloxy-4-methoxyanilino-N-(3-pyridylmethyl)-N-3-(4-pyridyl)benzamide

To a solution of N-(3-cyclopentyloxy-4-methoxyphenyl)-N-(3-pyridylmethyl)-3-aminobenzoic acid (20 mg, 0.05 mmol) and pyBOP (40 mg. 0.08 mmol) in CH$_2$Cl$_2$ (2 mL) at room temperature was added diisopropylethylamine (20 L, 0.1 mmol). After stirring for 15 min, 4-aminopyridine (15 mg, 0.15 mmol) was added and the mixture was allowed to stir 16 h. The mixture was diluted with EtOAc (25 mL) and washed with water (2×15 mL) and brine (15 mL), dried (MgSO$_4$), and concentrated in vacuo. The crude residue was loaded onto a RediSep column (4.2 g, silica gel) and the product was eluted with a linear gradient from 40% EtOAc in hexanes to 60% EtOAc in hexanes over 15 min to give 22 mg of product. $^1$H NMR (CDCl$_3$) δ8.70–8.40 (m, 3H), 8.24 (s, 1H), 7.72 (d, 1H, 9.0 Hz), 7.68–7.55 (m, 2H), 7.30–7.20 (m, 1H), 6.88 (d, 2H, J=8.5), 6.80–6.65 (m, 3H), 4.98 (s, 2H), 4.66 (p, 1H, J=4.1 Hz), 3.86 (s, 3H), 1.86–1.70 (m, 6H), 1.65–1.45 (m, 2H).

The following compounds were prepared in a similar manner as described above:

a) 3-(3-Cyclopentyloxy-4-methoxyanilino)-N-(3-pyridylmethyl)-N-3-[3-(N,N-dimethylamino)prop-1-yl]benzamide
b) 3-Cyclopentyloxy-4-methoxy-3'-(4-methylpiperazin-1-ylcarbonyl)-N-(3-pyridylmethyl)diphenylamine
c) 3-Cyclopentyloxy-4-difluoromethoxy-4'-(4-methylpiperazin-1-ylcarbonyl)-N-(3-pyridylmethyl) diphenylamine
d) 3-Cyclopentyloxy-4-methoxy-4'-(4-methylpiperazin-1-ylcarbonyl)-N-(3-piridylmethyl)-3-(3-tetrahydrofuranyloxy)-diphenylamine

EXAMPLE 11

The following compounds were prepared in a similar fashion as described in Example 2:

a) 4'-Amino-3-cyclopentyloxy-4-methoxy-N-(3-pyridylmethyl)diphenylamine
b) 3-Amino-3-cyclopentyloxy-4-methoxy-N-(3-pyridylmethyl)diphenylamine
c) 3'-Amino-3-cyclopropylmethoxy-4-methoxy-N-(3-pyridylmethyl)diphenylamine
d) 3'-Amino-4-methoxy-N-(3-pyridylmethyl)-3-[(3R)-tetrahydrofuryloxy]diphenylamine

EXAMPLE 12

3-Cyclopentyloxy-4'-methanesulfonylamino-4-methoxy-N-(3-pyridylmethyl)-diphenylamine To a solution of 4'-amino-3-cyclopentyloxy-4-methoxy-N-(3-pyridylmethyl)-idphenylamine (47 mg, 0.12 mmol) in CH$_2$Cl$_2$ (2 mL) at room temperature was added pyridine (20 microliters, 0.24 mmol) followed by methanesulfonyl chloride (15 microliters, 0.18 mmol) and the mixture was allowed to stand at room temperature for 16 h. The mixture was diluted with ether (50 mL) and washed with water (25 mL) and brine (25 mL), dried (MgSO$_4$), and concentrated. The crude residue was purified by flash column chromatography (4.2 g RediSep column, silica gel) eluting with a linear gradient from 45% EtOAc in hexanes to 60% EtOAc in hexanes over 20 min to yield 41 mg of product. $^1$H NMR (CDCl$_3$) δ8.51 (s, 1H), 8.41 (d, 1H, J=4.8 Hz), 7.56 (d, 1H, 7.9 Hz), 7.16 (m, 1H), 6.98 (d, 2H, J=9.0Hz), 6.80–6.60 (m, 6H), 4.82 (s, 2H), 4.56 (p, 1H), J=4.0 Hz), 3.75 (s, 3H), 2.86 (s, 3H), 1.86–1.70 (m, 6H), 1.65–1.45 (m, 2H).

The following compounds were prepared in a similar manner as described above:

a) 3-Cyclopentyloxy-3'-ethanesulfonylamino-4-methoxy-N-(3-pyridylmethyl)diphenylamine
b) 3-Cyclopentyloxy-4-methoxy-3'-(1-propanesulfonyl-amino)-N-(3-pyridylmethyl)diphenylamine
c) 3'-(1-Butanesulfonylamino)-3-cyclopentyloxy-4-methoxy-N-(3-pyridylmethyl)diphenylamine
d) 3'-Benzylsulfonylamino-3-cyclopentyloxy-4-methoxy-N-(3-pyridylmethyl)diphenylamine
e) 3'-Acetamido-3-cyclopentyloxy-4-methoxy-N-(3-pyridylmethyl)diphenylamine
f) 3-Cyclopentyloxy-4'-ethanesulfonylamino-4-methoxy-N-(3-pyridylmethyl)diphenylamine
g) 3-Cyclopentyloxy-4-methoxy-4'-(1-propanesulfonyl-amino)-N-(3-pyridylmethyl)diphenylamine
h) 3-Cyclopropylmethoxy-3'-ethanesulfonylamino-4-methoxy-N-(3-pyridylmethyl)diphenylamine
i) 4-Difluoromethoxy-3'-ethanesulfonylamino-N-(3-pyridylmethyl)-3-[(3R)-tetrahydrofuryloxy]diphenylamine

EXAMPLE 13

3-Cyclopentyloxy-4-methoxy-3'-hydroxymethyl-N-(3-pyridylmethyl)diphenylamine

To a solution of Ethyl N-(3-cyclopentyloxy-4-methoxyphenyl)-N-(3-pyridylmethyl)-3-aminobenzoate (50 mg, 0.11 mmol) in THF (5 mL) at 0° C. was added drop-wise, with stirring, 2.5M diisobutylaluminum hydride in toluene (0.4 mL, 1.00 mmol). The mixture was stirred at 0° C. for 1 h and the excess diisobutylaluminum hydride was quenched by adding 5 drops of EtOAc to the mixture. The mixture was concentrated and the residue was partitioned between $CH_2Cl_2$ (50 mL) and water (50 mL). The layers were separated and the aqueous layer was extracted with $CH_2Cl_2$ (2×10 mL). The organic extracts were combined and washed with brine (50 mL), dried ($MgSO_4$), and concentrated. The crude residue was purified by flash column chromatography (4.2 g RediSep column, silica gel) eluting with 300 mL 50% EtOAc in hexanes then 100% EtOAc to give 15 mg of product. $^1$H NMR ($CDCl_3$) δ8.51 (s, 1H), 8.40 (br, 1H), 7.58 (d, 1H, 7.9 Hz), 7.25–7.05 (m, 3H), 6.80–6.60 (m, 5H), 4.85 (s, 2H), 4.56 (p, 1H, J=4.1 Hz), 4.50 (s, 2H), 3.76 (s, 3H), 1.86–1.70 (m, 7H), 1.65–1.45 (m, 2H).

The following compounds were prepared in a similar manner as described above:

a) 3-Cyclopentyloxy-4-methoxy-4'-hydroxymethyl-N-(3-pyridylmethyl)diphenylamine

EXAMPLE 14

3-Cyclopentyloxy-4-methoxy-N-(3-pyridylmethyl)-4'-(2H-tetrazol-5-yl)diphenylamine To a solution of N-(3-cyclopentyloxy-4-methoxyphenyl)-N-(3-pyridylmethyl)-3-aminobenzonitrile (100 mg, 0.25 mmol) in DMF (3 mL) was added $NaN_3$ (163 mg, 2.5 mmol) and $NH_4Cl$ (135 mg, 2.5 mmol) and the mixture was stirred at 120° C. for 6 h. The mixture was cooled to room temperature, diluted with water (50 mL) and extracted with EtOAc (2×25 mL). The EtOAc extracts were combined, washed with water (25 mL) and brine (25 mL), dried ($MgSO_4$), and concentrated in vacuo. The residue was loaded onto a RediSep column (4.2 g, silica gel) and eluted with a linear gradient from 50% to 75% EtOAc in hexanes to yield 12 mg of product. $^1$H NMR ($CDCl_3$) δ12.50 (br, 1H), 8.64 (s, 1H), 8.54 (br, 1H), 7.86 (d, 2H, J=8.8 Hz), 7.75 (d, 1H, 7.8 Hz), 7.36 (m, 1H), 6.80–6.60 (m, 5H), 4.99 (s, 2H), 4.66 (p, 1H, J=4.1 Hz), 3.84 (s, 3H), 1.86–1.70 (m, 7H), 1.65–1.45 (m, 2H).

EXAMPLE 15

3-Cyclopentyloxy-4-methoxy-4'-(4-methyl-1-piperazinylmethyl)-N-(3-pyridylmethyl)diphenylamine To a solution of 3-cyclopentyloxy-4-methoxy-4'-(4-methylpiperazin-1-ylcarbonyl)dipheylamine (100 mg, 0.20 mmol) in THF (5 mL) was carefully added, with stirring, lithium aluminum hydride (50 mg, 1.3 mmol). The mixture was stirred for 15 min and a few drops of EtOAc was carefully added to quench the excess hydride. Water (50 mL) and $CH_2Cl_2$ (50 mL) were added and the mixtures were filtered through Celite. The $CH_2Cl_2$ layer was separated, washed with brine (25 mL), dried ($MgSO_4$), and concentrated in vacuo. The crude residue was purified on an ISCO RediSep column (4.2 g, silica) eluting with a gradient from 5% MeOH in EtOAc to 15% MeOH in EtOAc to yield 60 mg of product as a light yellow oil. $^1$H NMR ($CDCl_3$) δ8.59 (s, 1H), 8.47 (d, 1H, J=4.8 Hz), 7.65 (d, 1H, 7.9 Hz), 7.21 (dd, 1H, J=4.8 Hz, 7.9 Hz), 7.11 (d, 2H, J=8.6 Hz), 6.82–6.73 (m, 3H), 6.70–6.65 (m, 2H), 4.91 (s, 2H), 4.62 (p, 1H, J=4.12 Hz), 3.82 (s, 3H), 3.41 (s, 2H), 2.75–2.20 (m, 8H), 2.27 (s, 3H), 1.86–1.70 (m, 6H), 1.65–1.45 (m, 2H).

The following compounds were prepared in a similar manner as described above:

a) 3-Cyclopentyloxy-4-methoxy-3'-(4-methyl-1-piperazinylmethyl)N-(3-pyridylmethyl)diphenylamine

EXAMPLE 16

3'-Aminomethyl-3-cyclopentyloxy-4-methoxy-N-(3-pyridylmethyl)diphenylamine

To a solution of N-(3-cyclopentyloxy-4-methoxyphenyl)-N-(3-pyridylmethyl)-3-aminobenzonitrile (50 mg, 0.12 mmol) in THF (5 mL) was carefully added, with stirring, lithium aluminum hydride (20 mg, 0.52 mmol). The mixture was stirred for 4 h and a few drops of water were carefully added to quench the excess hydride. Water (50 mL) and $CH_2Cl_2$ (50 mL) were added and the mixtures were filtered through Celite. The $CH_2Cl_2$ layer was separated, washed with brine (25 mL), dried ($MgSO_4$), and concentrated in vacuo. The crude residue was purified on an ISCO RediSep column (4.2 g, silica) eluting with 10% MeOH in EtOAc to yield 20 mg of product. $^1$H NMR ($CDCl_3$) δ8.60 (s, 1H), 8.47 (br, 1H), 7.65 (d, 1H, 7.8 Hz), 7.26–7.10 (m, 2H), 6.90–6.65 (m, 6H), 4.94 (s, 2H), 4.63 (p, 1H, J=4.1 Hz), 3.83 (s, 3H), 3.75 (m, 2H), 2.29 (br, 2H), 1.86–1.70 (m, 6H), 1.65–1.45 (m, 2H).

EXAMPLE 17

3-Hydroxy-4-methoxy-N-(3-pyridylmethyl)diphenylamine

To a solution of 3-(tert-butyldimethylsiloxy)-N-(3-pyridylmethyl)-4-methoxydiphenylamine (1.20 g, 2.85 mmol) in THF (40 mL) at 0° C., was added 1.0M tetrabutylammonium fluoride in THF (10 mL, 10 mmol). The mixture was stirred at 0° C. for 30 min. Water (50 mL) was added and the mixture was extracted with ether (3×25 mL). The ether extracts were combined and washed with water (3×25 mL) and brine (25 mL), dried ($MgSO_4$), and concentrated in vacuo. The residue was triturated with hexanes and collected by vacuum filtration to give 0.85 g of product. $^1$H NMR ($CDCl_3$) δ8.58 (s, 1H), 8.46 (br, 1H), 7.67 (d, 1H, 7.8 Hz), 7.26–7.10 (m, 3H), 6.90–6.65 (m, 5H), 6.64 (dd, 1H, J=8.6 Hz, 2.6 Hz), 6.53 (br, 1H), 4.92 (s, 2H), 3.86 (s, 3H).

The following compounds were prepared in a similar manner as described above:

a) 3'-Chloro-3-hydroxy-4-methoxy-N-(3-pyridylmethyl)diphenylamine b) Ethyl N-(3-hydroxy-4-methoxyphenyl)-N-(3-pyridylmethyl)-3-aminobenzoate

EXAMPLE 18 (Method B)

The following compounds were prepared in a similar manner as described in Example 1B:

a) 3-[3-(4-Chlorophenyl)prop-1-yloxy]-4-methoxy-N-(3-pyridylmethyl)diphenylamine b) 3-[2-(4-Chlorophenyl)ethoxy]-4-methoxy-N-(3-pyridylmethyl)diphenylamine c) 4-Methoxy-3-(4-phenoxybut-1-yl)oxy-N-(3-pyridylmethyl)diphenylamine d) 4-Methoxy-N-(3-pyridylmethyl)-3-(3-tetrahydrofuryloxy)diphenylamine e) 4-Methoxy-3-[3-(4-methoxyphenyl)prop-1-yl]oxy-N-(3-pyridylmethyl)diphenylamine f) 4-Methoxy-3-[3-(4-pyridyl)prop-1-yl]oxy-N-(3-pyridylmethyl)diphenylamine g) 4-Methoxy-3-[2-(4-methoxyphenyl)ethoxy]-N-(3-pyridylmethyl)diphenylamine
h) 4-Methoxy-3-(4-phenylbut-1-yl)oxy-N-(3-pyridylmethyl)diphenylamine
i) 4-Methoxy-3-[4-(4-methoxyphenyl)but-1-yl]oxy-N-(3-pyridylmethyl)diphenylamine
j) 4-Methoxy-3-[4-(4-nitrophenyl)but-1-yl]oxy-N-(3-pyridylmethyl)diphenylamine
k) 4-Methoxy-3-[2-(2-pyridyl)ethoxy]-N-(3-pyridylmethyl)diphenylamine
l) 4-Methoxy-3-[2-(4-pyridyl)ethoxy]-N-(3-pyridylmethyl)diphenylamine
m) 4-Methoxy-3-[3-(2-pyridyl)prop-1-yl]oxy-N-(3-pyridylmethyl)diphenylamine
n) 4-Methoxy-3-(2-methoxyethoxy)-N-(3-pyridylmethyl)diphenylamine
o) 3-Cyclopropylmethoxy-4-methoxy-N-($^3$-pyridylmethyl)diphenylamine
p) 4-Methoxy-3-(1-methylpyrrolidin-3-yl)oxy-N-(3-pyridylmethyl)diphenylamine
q) 4-Methoxy-3-(1-methylpiperidin-4-yl)oxy-N-(3-pyridylmethyl)diphenylamine
r) 4-Methoxy-N-(3-pyridylmethyl)-3-[(3S)-tetrahydrofuryloxy]diphenylamine
s) 4-Methoxy-N-(3-pyridylmethyl)-3-[(3R)-tetrahydrofuryloxy]diphenylamine
t) 3'-Chloro-4-methoxy-3-[2-(2-pyridyl)ethoxy]-N-(3-pyridylmethyl)diphenylamine
u) 3'-Chloro-4-methoxy-3-[2-(4-pyridyl)ethoxy]-N-(3-pyridylmethyl)diphenylamine
v) 3'-Chloro-4-methoxy-3-(2-methoxyethoxy)-N-(3-pyridylmethyl)diphenylamine
w) 3'-Chloro-4-methoxy-N-(3-pyridylmethyl)-3-[($^3$R)-tetrahydrofuryloxy]diphenylamine
x) 3-Cyclohexyloxy-4-methoxy-N-(3-pyridylmethyl)diphenylamine
y) 3-Cycloheptyloxy-4-methoxy-N-(3-pyridylmethyl)diphenylamine
z) 3-(2-Cyclopropylethoxy)-4-methoxy-N-(3-pyridylmethyl)diphenylamine
aa) 3-Cyclopentylmethoxy-4-methoxy-N-(3-pyridyhnethyl)diphenylamine
bb) Ethyl N-[3-(4-chlorophenyl)prop-1-yloxy-4-methoxyphenyl]-N-(3-pyridylmethyl)-3-aminobenzoate
cc) Ethyl N-(3-cyclopropylmethoxy-4-methoxyphenyl)-N-(3-pyridylmethyl)-3-aminobenzoate
dd) Ethyl N-(3-cyclopropylmethoxy-4-difluoromethoxyphenyl)-N-(3-pyridylmethyl)-3-aminobenzoate
ee) Ethyl N-[3-(2-indanyloxy)-4-methoxyphenyl]-N-(3-pyridylmethyl)-3-aminobenzoate
ff) Ethyl N-[4-methoxy-3-(3-tetrahydrofuryloxy)phenyl]-N-(3-pyridylmethyl)-3-aminobenzoate
gg) Ethyl N-[4-methoxy-3-((3R)-tetrahydrofuryloxy)phenyl]-N-(3-pyridylmethyl)-3-aminobenzoate
hh) Ethyl N-[3-(2-methoxyethoxy)-4-methoxyphenyl]-N-(3-pyridylmethyl)-3-aminobenzoate
ii) Ethyl N-[4-methoxy-3-(2-(2-pyridyl)ethyl)oxyphenyl]-N-(3-pyridylmethyl)-3-aminobenzoate

EXAMPLE 18 (Method C)

The following compounds were prepared in a similar manner as described in Example 8A by coupling a phenol with a boronic acid rather than coupling an aniline with a boronic acid:

a) 4-Methoxy-3-(4-methoxyphenoxy)-N-(3-pyridylmethyl)diphenylamine
b) 4-Methoxy-3-phenoxy-N-(3-pyridylmethyl)diphenylamine
c) 4-Methoxy-3-(4-methylphenoxy)-N-(3-pyridylmethyl)diphenylamine
d) 3-(4-Chlorophenoxy)-4-methoxy-N-(3-pyridyhnethyl)diphenylamine
e) 3-[2-(4-Chlorophenyl)ethenyloxy]-4-methoxy-N-(3-pyridyhnethyl)diphenylamine

EXAMPLE 19

The following compounds were prepared in a similar manner as described in Example 17:

a) 3-Cyclopentyloxy-3'-hydroxy-4-methoxy-N-(3-pyridylmethyl)diphenylamine
b) 3-Cyclopentyloxy-4'-hydroxy-4-methoxy-N-(3-pyridylmethyl)diphenylamine
c) 3-Cyclopropylmethoxy-4'-hydroxy-4-methoxy-N-(3-pyridylmethyl)diphenylamine

EXAMPLE 20 (Method A)

The following compounds were prepared in a similar manner as described in Example 1A:

a) 3'-(2-Bromoethoxy)-3-cyclopentyloxy-4-methoxy-N-(3-pyridylmethyl)diphenylamine

EXAMPLE 20 (Method B)

The following compounds were prepared in a similar manner as described in Example 1B:

a) 3-Cyclopentyloxy-4'-(2-methoxyethoxy)-4-methoxy-N-(3-pyridylmethyl)diphenylamine
b) 3-Cyclopentyloxy-4'-(3-methyl-1-butoxy)-4-methoxy-N-(3-pyridylmethyl)diphenylamine
c) 3-Cyclopentyloxy-4-methoxy-N-(3-pyridylmethyl)-4'-[(3S)-tetrahydrofuranyloxy]-diphenylamine
d) 3-Cyclopentyloxy-4-methoxy-N-(3-pyridylmethyl)-4'-[(3R)-tetrahydrofuranyloxy]-diphenylamine
e) 3-Cyclopentyloxy-4'-cyclopropylmethoxy-4-methoxy-N-(3-pyridylmethyl)diphenylamine
f) 4'-Cyclohexylethoxy-3-cyclopentyloxy-4-methoxy-N-(3-pyridylmethyl)diphenylamine
g) 4'-Cyclopentylethoxy-3-cyclopentyloxy-4-methoxy-N-(3-pyridylmethyl)diphenylamine
h) 3-Cyclopentyloxy-4-methoxy-4'-(1-methylpiperidin-4-yloxy)-N-(3-pyridylmethyl)diphenylamine
i) 3-Cyclopentyloxy-4-methoxy-4'-(1-methylpyrrolidin-3-yloxy)-N-(3-pyridylmethyl)diphenylamine
j) 3-Cyclopentyloxy-4-methoxy-4'-[2-(1-methylpyrrolidin-2-yl)ethoxy]-N-(3-pyridylmethyl) diphenylamine
k) 3-Cyclopentyloxy-4-methoxy-4'-[2-(1-pyrrolidinylethoxy)-N-(3-pyridylmethyl)diphenylamine
l) 3-Cyclopentyloxy-4-methoxy-4'-[2-(6-methylpyridyl)methoxy)-N-(3-pyridylmethyl)diphenylamine
m) 3-Cyclopentyloxy-4-methoxy-4'-[3-(1-methylpiperidinyl)methoxy]-N-(3-pyridylmethyl) diphenylamine
n) 3-Cyclopentyloxy-4-methoxy-4'-[2-(1-methylpiperidinyl)methoxy]-N-(3-pyridylmethyl) diphenylamine
o) 3-Cyclopentyloxy-4-methoxy-4'-[2-(5-oxopyrrolidinyl)methoxy]-N-(3-pyridylmethyl)diphenylamine p) 4'-[1-(3-Bromopropyl)oxy]-3-cyclopentyloxy-4-methoxy-N-(3-pyridylmethyl)diphenylamine q) 3-Cyclopentyloxy-4-methoxy-4'-[2-(N-phthalimido)ethoxy]-N-(3-pyridylmethyl)diphenylamine

EXAMPLE 21

3-Cyclopentyloxy-4-methoxy-3'-[2-(1-piperidinyl)ethoxyl-N-(3-pyridylmethyl)diphenylamine To a solution of 3'-(2-bromoethoxy)-3-cyclopentyloxy-4-methoxy-N-(3-pyridylmethyl)diphenylamine (17 mg, 0.03 mmol) in acetonitrile (1 mL) was added potassium carbonate (25 mg, 0.18 mmol) and piperidine (5 µL, 0.05 mmol) and the mixture was stirred at 60° C. for 4 h. The mixture was partitioned between water (50 mL) and EtOAc (50 mL). The layers were separated and the organic layer was washed with water (25 mL) and brine (25 mL), dried (MgSO$_4$), and concentrated in vacuo. The residue was loaded on an ISCO RediSep column (4.2 g, silica) and the column was eluted with a linear gradient from 5% MeOH in EtOAc to 15% MeOH in EtOAc to give 11 mg of product. $^1$H NMR (CDCl$_3$) δ8.59 (s, 1H), 8.48 (d, 1H, J=4.7), 7.64 (d, 1H, 8.2 Hz), 7.26–7.20 (m, 1H), 7.06 (t, 1H, J=8.6 Hz), 6.81 (d, 1H, J=9.2 Hz), 6.75–6.68 (m, 2H), 6.45–6.35 (m, 3H), 4.91 (s, 2H), 4.64 (p, 1H, J=4.1 Hz), 4.00 (t, 2H, J=6.2 Hz), 3.84 (s, 3H), 2.71 (t, 2H, J=6.2 Hz), 2.47 (m, 4H), 1.90–1.70 (m, 6H), 1.86–1.70 (m, 6H), 1.65–1.45 (m, 2H).

The following compounds were prepared in a similar manner as described above:

a) 3-Cyclopentyloxy-3'-[2-(1-imidazolyl)ethoxy]-4-methoxy-N-(3-pyridylmethyl)diphenylamine b) 3-Cyclopentyloxy-4-methoxy-3'-[2-(1-methylpiperazin-4-yl)ethoxy]-N-(3-pyridylmethyl) diphenylamine c) 3-Cyclopentyloxy-4-methoxy-4'-[3-(2-methylpiperazin-4-yl)propoxy]-N-(3-pyridylmethyl) diphenylamine d) 3-Cyclopentyloxy-4-methoxy-4'-[3-(1-methylpiperazin-4-yl)propoxy]-N-(3-pyridylmethyl) diphenylamine e) 3-Cyclopentyloxy-4-methoxy-4'-[3-(2-morpholin-4-ylethylamino)propoxy]-N-(3-pyridylmethyl)diphenylamine f) 4-Methoxy-3-(2-phenoxyethoxy)-N-(3-pyridylmethyl)diphenylamine g) 3-[2-(4-Chlorophenoxy)ethoxy]-4-methoxy-N-(3-pyridylmethyl)diphenylamine h) 4-Methoxy-3-(2-pyrrolidin-1-yl)ethoxy-N-(3-pyridylmethyl)diphenylamine i) 4-Methoxy-3-(2-(4-methylpiperazin-1-yl)ethoxy)-N-(3-pyridylmethyl)diphenylamine j) 3-[2-(4-Chlorophenylamino)ethoxy]-4-methoxy-N-(3-pyridylmethyl)diphenylamine

EXAMPLE 22

4'-Aminoethoxy-3-cyclopentyloxy-4-methoxy-N-(3-pyridylmethyl)diphenylamine

To a solution of N-(3-pyridylmethyl)-3'-[2-(2-phthalimido)ethoxy]-3-cyclopentyloxy-4-methoxydiphenylamine (0.39 g, 0.69 mmol) in MeOH (5 mL) was added hydrazine hydrate (1.0 mL, 20 mmol). After 6 h at room temperature, EtOAc was added (50 mL) and the precipitate was filtered off. The filtrate was washed with water (25 mL) and brine (25 mL), dried (MgSO$_4$), and concentrated in vacuo. The residue was loaded on an ISCO RediSep column (10 g, silica). The column was washed with 10% MeOH in EtOAc (200 mL) and the product was eluted with 50% MeOH in EtOAc to yield 0.21 g. $^1$H NMR (CDCl$_3$) δ8.55 (s, 1H), 8.42 (d, 1H, J=3.8 Hz), 7.62 (d, 1H, 7.7 Hz), 7.20–7.10 (m, 1H), 6.91 (d, 2H, J=9.0 Hz), 6.78 (d, 2H, J=9.0 Hz), 6.70 (d, 1H, J=8.6 Hz), 6.50–6.35 (m, 2H), 4.82 (s, 2H), 4.54 (p, 1H, J=4.1 Hz), 3.90 (t, 2H, J=56.1 Hz), 3.74 (s, 3H), 3.01 (m, 2H), 1.86–1.70 (m, 8H), 1.65–1.45 (m, 2H).

EXAMPLE 23

The following compounds were prepared in a similar manner as described in Example 12:

a) 3-Cyclopentyloxy-4'-(2-methanesulfonylamino)ethoxy-4-methoxy-N-(3-pyridylmethyl)diphenylamine b) 3-Cyclopentyloxy-4'-(2-ethanesulfonylamino)ethoxy-4-methoxy-N-(3-pyridylmethyl)diphenylamine c) 3-Cyclopentyloxy-4-methoxy-4'-[2-(2-propanesulfonylamino)ethoxy]-N-(3-pyridylmethyl) diphenylamine d) 3-Cyclopentyloxy-4-methoxy-4'-[2-(1-propanesulfonylamino)ethoxy]-N-(3-pyridylmethyl) diphenylamine e) 4'-[2-(1-Butanesulfonylamino)ethoxy]-3-cyclopentyloxy-4-methoxy-N-(3-pyridylmethyl) diphenylamine

EXAMPLE 24

In Vitro Measurement of Type 4 Phosphodiesterase Inhibition Activity

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 mM MgCl$_2$, 3 uM cAMP, 0.002 U 5'-nucleotidase, and 3×10$^4$ cpm of [3H]cAMP. The reaction was stopped by adding 100 µl of boiling 5 mN HCl. An aliquot of 75 µl of reaction mixture was transferred from each well to alumina columns (Multiplate; Millipore). Labeled adenosine was eluted into an OptiPlate by spinning at 2000 rpm for 2 min; 150 µl per well of scintillation fluid was added to the OptiPlate. The plate was sealed, shaken for about 30 min, and cpm of [$^3$H]adenosine was determined using a Wallac Triflux®.

All test compounds are dissolved in 100% DMSO and diluted into the assay such that the final concentration of DMSO is 0.1%. DMSO does not affect enzyme activity at this concentration.

A decrease in adeno sine concentration is indicative of inhibition of PDE activity. $pIC_{50}$ values were determined by screening 6 to 12 concentrations of compound ranging from 0.1 nM to 10,000 nM and then plotting drug concentration versus $^3$H-adenosine concentration. Nonlinear regression software (Assay Explorer®) was used to estimate $pIC_{50}$ values.

EXAMPLE 25 (Method A)

Passive Avoidance in Rats, an in vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Sprague-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg MK-801 or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naïve rats required less than 30 seconds, on average, to cross from the illuminated compartment to the darkened compartment. However, 24 hours after the electric shock exposure, most rats pretreated with vehicle did not re-enter the darkened compartment; the average latency was increased up to 175 seconds (p<0.001). Pretreatment with MK-801 (0.1 mg/kg) markedly reduced this latency when compared to the vehicle p<0.001). This amnesic effect of MK-801 is reversed in a statistically significant manner by actual test compounds in a dose-dependent fashion (e.g., 3-cyclopentyloxy-4-methoxy-N-(3-pyridylmethyl) diphenylamine, Effective dose range=0.5 to 2.5 mg/kg, i.p.; and N-(3-cyclopentyloxy-4-methoxyphenyl)-N-(3-pyridylmethyl)-3-aminobenzoic acid, effective dose range=0.1 to 2.5 mg/kg, ip).

EXAMPLE 25 (Method B)

Radial arm maze task in Rats, an in vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198–204.). Five days after initial housing, rats (male Sprague-Dawley (Harlan) weighing 250 to 350 g) were placed in the eight-arm radial maze (each arm was 60×10× 12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. MK-801 or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests. Compared to control, MK-801 (0.1 mg/kg, i.p.) increased the frequencies of both working and reference memory errors (p<0.01). This amnesic effect of MK-801 on working memory is reversed in a statistically significant manner by the administration of actual test compounds in a dose-dependent fashion (e.g., 3-cyclopentyloxy-4-methoxy-N-(3-pyridylmethyl)diphenylamine, Effective dose=2.5 mg/kg, i.p.; p<0.01)

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

What is claimed is:

1. A compound at Formula I

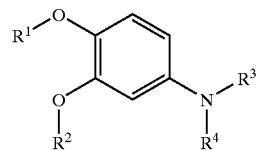

wherein:
R$^1$ is alkyl having 1 to 4 carbon atoms, which is branched or unbranched and which is unsubstituted or substituted one or more times by halogen;
R$^2$ is cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof;
R$^3$ is heteroarylalkyl wherein die hetereoaryl portion is furyl, thienyl, pyrrolyl, pyrazolyl, imidazolyl, triazolyl, tetrazolyl, dithialyl, oxathialyl, isoxazolyl, oxazolyl, thiazolyl, isothiazolyl, oxadiazolyl, oxadiazolyl, dioxazolyl, oxathiazalyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, or benzoxazinyl, and wherein the alkyl portion, which is branched or unbranched, has 1 to 5 carbon atoms, the heteroarylalkyl group is unsubstituted or substituted one or more times in the hereroaryl portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof;

$R^4$ is aryl having 6 to 14 carbon atoms and which is unsubstituted or substituted one or more limes by halogen, alkyl, alkenyl, alkynyl, hydroxy, alkoxy, alkoxyalkoxy, intro, methylenedioxy, ethylenedioxy, trifluoromethyl, $OCF_3$, amino, aminoalkyl, aminoalkoxy, dialkylamino, hydroxyalkyl, hydroxamic acid, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof;

$R^5$ is H,
alkyl having 1 to 8 carbon atoms, which is unsubstituted or substituted one or more times with halogen, $C_{1-4}$-alkyl, $C_{1-4}$-alkoxy, oxo, or combinations thereof, alkylamino or dialkylamino wherein each alkyl portion has independently 1 to 8 carbon atoms, a partially unsaturated carbocycle-alkyl group wherein the portion has 5 to 14 carbon atoms and the alkyl portion has 1 to 5 carbon atoms, which is unsubstituted or substituted one or more times by halogen, alkyl, alkoxy, nitro, cyano, oxo, or combinations thereof, cycloalkyl having 3 to 10 carbon atoms, which is unsubstituted or substituted one or more dines by halogen, hydroxy, oxo, cyano, alkoxy, alkyl having 1 to 4 carbon atoms, or combinations thereof, cycloalkylalkyl having 4 to 16 carbon atoms, which is unsubstituted or substituted in the cycloalkyl portion and/or the alkyl portion one or more times by halogen, oxo, cyano, hydroxy, alkyl, alkoxy or combinations thereof, aryl having 6 to 14 carbon atoms and which is unsubstituted or substituted one or more tunes by halogen, alkyl, hydroxy, alkoxy, alkoxyalkyl, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, or combinations thereof or arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, intro, amino, alkyl, alkoxy, amino, alkylamino, dialkylamino and/or substituted in the alkyl portion by halogen, cyano, or methyl;

L is a single bond or a divalent aliphatic radical having 1 TO 8 carbon atoms wherein one or more —$CH_2$— groups are each optionally replaced by —O—, —S—, —$NR^6$—, —$SO_2NH$—, —$NHSO_2$—, —CO—, —$NR^6CO$—, —$CONR^6$—, —NHCONH—, —OCONH, —NHCOO—, —SCONH—, —SCSNH—, or —NHCSNH—; and $R^6$ is H, or
alkyl having 1 to 8 carbon atoms, which is branched or unbranched and which is unsubstituted or substituted one or more times with halogen, $C_{1-4}$-alkyl, $C_{1-4}$-alkoxy, oxo, or combinations thereof; or a pharmaceutically acceptable salt thereof.

2. A compound according to claim 1, wherein $R^1$ is methyl or $CHF_2$.

3. A compound according to claim 1, wherein $R^1$ is methyl or $CHF_2$ and $R^3$ is cyclopentyl.

4. A compound according to claim 1, wherein $R^1$ is methyl and $R^2$ is cyclopentyl.

5. A compound according to claim 1, wherein $R^1$ is methyl; $R^2$ is cyclopentyl; and $R^4$ is phenyl which is substituted or unsubstituted.

6. A compound according to claim 1, wherein $R^1$ is methyl; $R^2$ is cyclopentyl; $R^3$ is pyridylmethyl, pyrimidinylmethyl, thienylmethyl, pyridylpropyl, or pyrazinylmethyl, which in each case is substituted or unsubstituted, and $R^4$ is phenyl or phenyl substituted with 1 to 3 substituents.

7. A compound according to claim 1, wherein $R^1$ is methyl; $R^2$ is cyclopentyl; $R^3$ is pyridyhnethyl, pyrimidinylmethyl, thienylmethyl, pyridylpropyl, or pyrazinylmethyl, which in each case is substituted or unsubstituted; and $R^4$ is phenyl, naphthyl, or biphenyl, which in each case substituted or unsubstituted.

8. A compound according so claim 1, wherein said compound is of formula IV

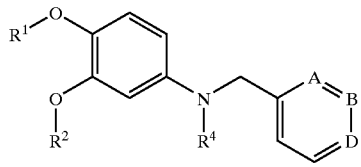

IV wherein $R^1$ and $R^2$ are as defined, a; least one of A, B, and D is N and the others are CH, and $R^4$ is phenyl which is each case is substituted or unsubstituted, and pharmaceutically acceptable salts thereof.

9. A compound according to claim 8, wherein $R^1$ is methyl or $CHF_2$.

10. A compound according to claim 9, wherein B is N.

11. A compound according to claim 8, wherein $R^1$ is methyl or $CHF_2$, and $R^2$ cyclopentyl.

12. A compound according to claim 11, wherein B is N.

13. A compound according to claim 8, wherein $R^1$ is methyl or $CHF_2$ and $R^4$ is phenyl, which is substituted or unsubstituted.

14. A compound according to claim 13, wherein B is N.

15. A compound according to claim 8, wherein $R^1$ is methyl or $CHF_2$, and $R^2$ is cyclopentyl, and $R^4$ is phenyl, which is substituted or unsubstituted.

16. A compound according to claim 15, wherein B is N.

17. A compound according claim 8, wherein $R^1$ is methyl or $CHF_2$, and it phenyl which is substituted in the 3- or 4-position.

18. A compound according to claim 17, wherein B is N.

19. A compound according to claim 8, wherein $R^1$ is methyl or $CHF_2$, $R^2$ is cyclopentyl and $R^4$ is phenyl which is substituted in the 3- or 4-position.

20. A compound according to claim 19, wherein B is N.

21. A compound according to claim 8, wherein R¹ is methyl or CHF₂, and R⁴ is 3-COOH-phenyl, 3-Cl-phenyl, 3-cyano-phenyl, 3-ethyl-sulfonamido-phenyl, 3-hydroxymethyl-phenyl, 3-nitro-phenyl, 4-COOH-phenyl, 4-cyano-phenyl, 4-ethyl-sulfonamido-phenyl, or 4-hydroxymethyl-phenyl.

22. A compound according to claim 21, wherein B is N.

23. A compound according to claim 8, wherein R¹ is methyl or CHF₂, R² is cyclopentyl and R⁴ is 3-COOH-phenyl, 3-Cl-phenyl, 3-cyano-phenyl, 3-ethyl-sulfonamido-phenyl, 3-hydroxymethyl-phenyl, 3-nitro-phenyl, 4-COOH-phenyl, 4-cyano-phenyl, 4-ethyl-sulfonamido-phenyl, or 4-hydroxymethyl-phenyl.

24. A compound according to claim 23, wherein B is N.

25. A compound according to claim 1, wherein said compound is selected from:
a) 3-Cyclopentyloxy-4'-ethyl-4-methoxy-N-(3-pyridylmethyl)diphenylamine
b) 3-Cyclopentyloxy-3',4-dimethoxy-N-(3-pyridylmethyl)diphenylamine
c) 3-Cyclopentyloxy-4-methoxy-N-(3-pyridylmethyl)-3'-trifluoromethyldiphenylamine
d) 3-Cyclopentyloxy-3'-fluoro-4-methoxy-N-(3-pyridylmethyl)diphenylamine
e) 3-Cyclopentyloxy-4'-fluoro-4-methoxy-N-(3-pyridylmethyl)diphenylamine
f) 3-Cyclopentyloxy-4-methoxy-3'-phenyl-N-(3-pyridylmethyl)diphenylamine
g) 4'-Cyano-3-cyclopentyloxy-4-methoxy-N-(3-pyridylmethyl)diphenylamine
h) 3-Cyclopentyloxy-4-methoxy-N-(3-pyridylmethyl)diphenylamine
i) 4'-Chloro-3-cyclopentyloxy-4-methoxy-N-(3-pyridylmethyl)-3'-trifluoromethyldiphenylamine
j) 3-Cyclopentyloxy-4-difluoromethoxy-N-(3-pyridylmethyl)diphenylamine
k) 3'-Benzylsulfonylamino-3-cyclopentyloxy-4-methoxy-N-(3-pyridylmethyl)diphenylamine
l) 3-Cyclopentyloxy-4'-(2-methoxy)-4-methoxy-N(3-pyridylmethyl)diphenylamine
m) 3-Cyclopentyloxy-4'-(2-methanesulfonylamino)ethoxy-4-methoxy-N-(3-pyridylmethyl)diphenylamine
n) 4'-[2-(1-Butanesulfonylamino)ethoxy]-3-cyclopentyloxy-4-methoxy-N-(3-pyridylmethyl)diphenylamine
o) 3-Cyclopentyloxy-4-methoxy-N-(3-pyridylmethyl)diphenylamine
p) 3-Cyclopentyloxy-4-methoxy-3'-methyl-N-(3-pyridylmethyl)diphenylamine
q) 3-Cyclopentyloxy-4-methoxy-4'-methyl-N-(3-pyridylmethyl)diphenylamine
r) 3-Cyclopentyloxy-4-methoxy-4'-nitro-N-(3-pyridylmethyl)diphenylamine
s) 3-Cyclopentyloxy-3',4-dichloro-4-methoxy-N-(3-pyridylmethyl)diphenylamine
t) 3'-Chloro-3-cyclopentyloxy-4'-fluoro-4-methoxy-N-(3-pyridylmethyl)diphenylamine
u) 3-Cyclopentyloxy-N-(2,6-dichloro-4-pyridylmethyl)-4-methoxydiphenylamine
v) 3'-(1-Butanesulfonylamino)-3-cyclopentyloxy-4-methoxy-N-(3-pyridylmethyl)diphenylamine
w) 3'-Acetamido-3-cyclopentyloxy-4-methoxy-N-(3-pyridylmethyl)diphenylamine
x) 3-Cyclopentyloxy-3'-hydroxy-4-methoxy-N-(3-pyridylmethyl)diphenylamine
y) 3-Cyclopentyloxy-3'-hydroxy-4-methoxy-N-(3-pyridylmethyl)diphenylamine
z) 4'-Cyclohexylethoxy-3-cyclopentyloxy-4-methoxy-N-(3-pyridylmethyl)diphenylamine
aa) 3-Cyano-3-cyclopentyloxy-4-methoxy-4'-[2-(2-propanesulfonylamino)ethoxy]-N-(3-pyridylmethyl)diphenylamine
bb) 3'-Cyano-3-cyclopentyloxy-4-methoxy-N-(3-pyridylmethyl)diphenylamine
cc) 4'-Chloro-3-cyclopentyloxy-3'-fluoro-4-methoxy-N-(3-pyridylmethyl)diphenylamine
dd) 3-Cyclopropylmethoxy-4-difluoromethoxy-N-(3-pyridylmethyl)diphenylamine
dd) 3 Cyclopropylmethoxy-4-difluoromethoxy-N-(3-pyridylmethyl)diphenylamine
ee) 3-Cyclopentyloxy-4-methanesulfonylamino-4-methoxy-N-(3-pyridylmethyl)-diphenylamine
ff) 3-Cyclopentyloxy-4-methoxy-3'-hydroxymethyl-N-(3-pyridylmethyl)diphenylamine
gg) 3-Cyclopentyloxy-4-methoxy-4-methoxy-4'-hydroxymethyl-N-(3-pyridylmethyl)diphenylamine
hh) 3-Cyclopentyloxy-4'-(2-ethanesulfonylamino)ethoxy-4-methoxy-N-(3-pyridylmethyl)diphenylamine
ii) 3-Cyclopentyloxy-4-methoxy-4'-[2-(1-propanesulfonylamino)ethoxy]-N-(3-pyridylmethyl)diphenylamine
jj) 3'-Chloro-3-cyclopentyloxy-4-methoxy-N-(3-pyridylmethyl)diphenylamine
kk) 4'-tert-Butyldimethylsilyloxy-3-cyclopentyloxy-4-methoxy-N-(3-pyridylmethyl)diphenylamine
ll) N-(3-Cyclopentyloxy-4-methoxyphenyl)-N-(3-pyridylmethyl)-3-aminobenzoic acid
mm) N-(3-Cyclopentyloxy-4-methoxyphenyl)-N-(3-pyridylmethyl)-3-aminobenzoic aminobenzoic acid
nn) N-(3-Cyclopentyloxy-4-difluoromethoxyphenyl)-N-(3-pyridylmethyl)-3-aminobenzoic acid
oo) 3-Cyclopentyloxy-3'-ethanesulfonylamino-4-methoxy-N-(3-pyridylmethyl)diphenylamine
pp) 3-Cyclopentyloxy-4-methoxy-3'-(1-propanesulfonylamino)-N-(3-pyridylmethyl)diphenylamine
qq) 3-Cyclopentyloxy-4'-ethanesulfonylamino-4-methoxy-N-(3-pyridylmethyl)diphenylamine
rr) 3-Cyclopentyloxy-4-methoxy-4'-(1-propanesulfonylamino)-N-(3-pyridylmethyl)diphenylamine
ss) 3-Cyclopropylmethoxy-3'-ethanesulfonylamino-4-methoxy-N-(3-pyridylmethyl)diphenylamine; and pharmaceutically acceptable salts thereof.

26. A compound according to claim 1, wherein said compound is selected from:
a) 3-Cyclopentyloxy-4-methoxy-N-(3-pyridylmethyl)diphenylamine
b) 3-Cyclopentyloxy-4-methoxy-3'-methyl-N-(3-pyridylmethyl)diphenylamine
c) 3-Cyclopentyloxy-4-methoxy-4'-methyl-N-(3-pyridylmethyl)diphenylamine
d) 3-Cyclopentyloxy-4-methoxy-4'-nitro-N-(3-pyridylmethyl)diphenylamine
e) 3-Cyclopentyloxy-3',4'-dichloro-4-methoxy-N-(3-pyridylmethyl)diphenylamine
f) 3'-Chloro-3-cyclopentyloxy-4'-fluoro-4-methoxy-N-(3-pyridylmethyl)diphenylamine g) 3-Cyclopentyloxy-N-(2.6-dichloro-4-pyridylmethyl)-4-methoxydiphenylamine
h) 3'-(1-Butanesulfonylamino)-3-cyclopentyloxy-4-methoxy-N-(3-pyridylmethyl)diphenylamine
i) 3'-Acetamido-3-cyclopentyloxy-4-methoxy-N-(3-pyridylmethyl)diphenylamine
j) 3-Cyclopentyloxy-3'-hydroxy-4-methoxy-N-(3-pyridylmethyl)diphenylamine
k) 3-Cyclopentyloxy-4'-hydroxy-4-methoxy-N-(3-pyridylmethyl)diphenylamine
l) 4'-Cyclohexylethoxy-3-cyclopentyloxy-4-methoxy-N-(3-pyridylmethyl)diphenylamine
m) 3-Cyclopentyloxy-4-methoxy-4-[2-(2-propanesulfonylamino)ethoxy]-N-(3-pyridylmethyl)diphenylamine
n) 3'-Cyano-3-cyclopentyloxy-4-methoxy-N-(3-pyridylmethyl)diphenylamine
o) 4'-Chloro-3-cyclopentyloxy-3'-fluoro-4-methoxy-N-(3-pyridylmethyl)diphenylamine
p) 3-Cyclopentyloxy-4'-methanesulfonylamino-4-methoxy-N-(3-pyridylmethyl)-diphenylamine
q) 3-Cyclopentyloxy-4-methoxy-3'-hydroxymethyl-N-(3-pyridylmethyl)diphenylamine
r) 3-Cyclopentyloxy-4-methoxy-4'-hydroxymethyl-N-(3-pyridylmethyl)diphenylamine
s) 3-Cyclopropylmethoxy-4'-hydroxy-4-methoxy-N-(3-pyridylmethyl)diphenylamine
t) 3-Cyclopentyloxy-4'-(2-ethanesulfonylamino)ethoxy-4-methoxy-N-(3-pyridylmethyl)diphenylamine
u) 3-Cyclopentyloxy-4-methoxy-4'-[2-(1-propanesulfonylamino)ethoxy]-N-(3-pyridylmethyl)diphenylamine
v) 3'-Chloro-3-cyclopentyloxy-4-methoxy-N-(3-pyridylmethyl)diphenylamine
w) 4'-tert-Butyldimethylsilyloxy-3-cyclopentyloxy-4-methoxy-N-(3-pyridylmethyl)diphenylamine
x) N-(3-Cyclopentyloxy-4-methoxyphenyl)-N-(3-pyridylmethyl)-3-aminobenzoic acid
y) N-(3-Cyclopentyloxy-4-methoxyphenyl)-N-(3-pyridylmethyl)-4-aminobenzoic acid
z) N-(3-Cyclopentyloxy-4-difluoromethoxyphenyl)-N-(3-pyridylmethyl)-3-aminobenzoic acid
aa) N-(3-Cyclopropylmethoxy-4-methoxyphenyl)-N-(3-pyridylmethyl)4-aminobenzoic acid
bb) N-(3-Cyclopropylmethoxy-4-difluoromethoxyphenyl)-N-(3-pyridylmethyl-3-aminobenzoic acid
cc) N-(3-Cyclopropylmethoxy-4-methoxyphenyl)-N-(3-pyridylmethyl)-3-aminobenzoic acid
dd) 3-Cyclopentyloxy-3'-ethanesulfonylamino-4-methoxy--N-(3-pyridylmethyl)diphenylamine
ee) 3-Cyclopentyloxy-4-methoxy-3'-(1-propanesulfonylamino)-N-(3-pyridylmethyl)diphenylamine
ff) 3-Cyclopentyloxy-4'-ethanesulfonylamino-4-methoxy-N-(3-pyridylmethyl)diphenylamine
gg) 3-Cyclopentyloxy-4-methoxy-4'-(1-propanesulfonylamino)-N-(3-pyridylmethyl)diphenylamine
hh) 3-Cyclopropylmethoxy-3'-ethanesulfonylamino-4-methoxy-N-(3-pharmaceutically acceptable salts thereof.

27. A compound according to claim 1, wherein said compound is selected from:
a) 3'-Cyano-3-cyclopentyloxy-4-methoxy-N-(3-pyridylmethyl)diphenylamine
b) 4'-Chloro-3-cyclopentyloxy-3'-fluoro-4-methoxy-N-(3-pyridylmethyl)diphenylamine
c) 3-Cyclopropylmethoxy-4-difluoromethoxy-N-(3-pyridylmethyl)diphenylamine
d) 3-Cyclopentyloxy-4'-methanesulfonylamino-4-methoxy-N-(3-pyridylmethyl)-diphenylamine
e) 3-Cyclopentyloxy-4-methoxy-3'-hydroxymethyl-N-(3-pyridylmethyl)diphenylamine
f) 3-Cyclopentyloxy-4-methoxy-4'-hydroxymethyl-N-(3-pyridylmethyl)diphenylamine
g) 3-Cyclopentyloxy-4'-(2-ethanesulfonylamino)ethoxy-4-methoxy-N-(3-pyridylmethyl)diphenylamine
h) 3-Cyclopentyloxy-4-methoxy-4'-[2-(1-propanesulfonylamino)ethoxy]-N-(3-pyridylmethyl)diphenylamine
i) 3'-Chloro-3-cyclopentyloxy-4-methoxy-N-(3-pyridylmethyl)diphenylamine
j) 4'-tert-Butyldimethylsilyloxy-3-cyclopentyloxy-4-methoxy-N-(3-pyridylmethyl)diphenylamine
k) N-(3-Cyclopentyloxy-4-methoxyphenyl)-N-(3-pyridylmethyl)-3-aminobenzoic acid
l) N-(3-Cyclopentyloxy-4-methoxyphenyl)-N-(3-pyridylmethyl)-4-aminobenzoic acid
m) N-(3-Cyclopentyloxy-4-difluoromethoxyphenyl)-N-(3-pyridylmethyl)-3-aminobenzoic acid
n) N-(3-Cyclopropylmethoxy-4-methoxyphenyl)-N-(3-pyridylmethyl-4-aminobenzoic acid
o) N-(3-Cyclopropylmethoxy-4-difluoromethoxyphenyl)-N-(3-pyridylmethyl)-3-aminobenzoic acid
p) N-(3-Cyclopropylmethoxy-4-methoxyphenyl)-N-(3-pyridylmethyl)-3-aminobenzoic acid
q) 3-Cyclopentyloxy-3'-ethanesulfonylamino-4-methoxy-N-(3-pyridylmethyl)diphenylamine
r) 3-Cyclopentyloxy-4-methoxy-3'-(1-propanesulfonylamino)-N-(3-pyridylmethyl)diphenylamine
s) 3-Cyclopentyloxy-4'-ethanesulfonylamino-4-methoxy-4-N-(3-pyridylmethyl)diphenylamine
t) 3-Cyclopentyloxy-4-methoxy-4'-(1-propanesulfonylamino)-N-(3-pyridylmethyl)diphenylamine; and pharmaceutically acceptable salts thereof.

28. A compound according to claim 1, wherein said compound is selected from:
a) 3'-Chloro-3-cyclopentyloxy-4-methoxy-N-(3-pyridylmethyl)diphenylamine
b) 4'-tert-Butyldimethylsilyloxy-3-cyclopentyloxy-4-methoxy-N-(3-pyridylmethyl)diphenylamine
c) N-(3-Cyclopentyloxy-4-methoxyphenyl)-N-(3-pyridylmethyl)-3-aminobenzoic acid
d) N-(3-Cyclopentyloxy-4-methoxyphenyl)-N-(3-pyridylmethyl-4-aminobenzoic acid
e) N-(3-Cyclopentyloxy-4-difluoromethoxyphenyl)-N-(3-pyridylmethyl-3-aminobenzoic acid
f) 3-Cyclopentyloxy-3'-ethanesulfonylamino-4-methoxy--N-(3-pyridylmethyl)diphenylamine
g) 3-Cyclopentyloxy-4-methoxy-3'-(1-propanesulfonylamino)-N-(3-pyridylmethyl)diphenylamine
h) 3-Cyclopentyloxy-4'-ethanesulfonylamino-4-methoxy-N-(3-pyridylmethyl)diphenylamine
i) 3-Cyclopentyloxy-4-methoxy-4'-(1-propanesulfonylamino)-N-(3-pyridylmethyl)diphenylamine; and pharmaceutically acceptable salts thereof.

29. A compound according to formula I':

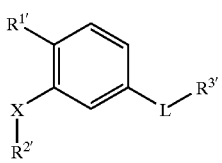

wherein
R¹' is methoxy;
R²'
cycloalkyl having 3 to 10 carbon atoms, or
cycloalkyl having 3 to 10 carbon atoms substituted one or more times by halogen, oxo, alkyl, or combinations thereof;
X is O;
R³ is heteroaryl selected from furyl, thienyl, pyrrolyl, pyrazolyl, imidazolyl, triazolyl, terrazolyl, dithialyl, oxathialyl, isoxazolyl, oxazolyl, thiazolyl, isothiazolyl, oxadiazolyl, oxatriazolyl, dioxazolyl, oxahiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isotionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, or substituted heteroaryl selected from furyl, thienyl, pyrrolyl, pyrazolyl, imidazolyl, triazolyl, terrazolyl, dithialyl, oxathialyl, isoxazolyl, oxazolyl, thiazolyl, isothiazolyl, oxadiazolyl, oxadiazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxadiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl winch is substituted one or more times by halogen, aryl, alkyl, alkoxy, cyano, trifluoromethyl, nitro, oxo, amino, alkylamino, dialkylamino or combinations thereof;
L is —NR⁴'CH₂—; and
R⁴ is aryl having 6 to 14 carbon atoms and which is unsubstituted or substituted one or more times by halogen, alkyl, hydroxy, alkoxy, nitro, methylenedioxy, ethylenedioxy, amino, alkylamino, dialkylamino, hydroxyalkyl, hydraxyalkoxy, carboxy, cyano, acyl, alkoxycarbonyl, alkylthio, alkylsulfinyl, alkylsulfonyl, phenoxy or combinations thereof; or a pharmaceutically acceptable salt thereof.

30. A method for enhancing cognition in a patient in wham such enhancement is desired comprising administering to said patient an effective amount of a compound according to claim 1.

31. A method according to claim 30, wherein said compound is administered in a amount of 0.01–100 mg/kg of body weight/day.

32. A method according to claim 30, wherein said patient is a human.

33. A method of treating a patient suffering from cognition impairment or decline comprising administering to said patient an effective amount of a compound according to claim 1.

34. A method according to claim 33, wherein said patient is a human.

35. A method according to claim 34, wherein said patient is suffering from memory impairment.

36. A method according to claim 33, wherein said compound is administered in an amount of 0.01–100 mg/kg of body weight/day.

37. A method according to claim 35, wherein said patient is suffering from memory impairment Alzheimer's disease, schizophrenia, Parkinson's disease, Huntington's disease, Pick's disease, Creutzfeld-Jakob disease, depression, aging, head trauma, stroke, CNS hypoxia, cerebral senility, multi-infaret dementia, HIV or cardiovascular disease.

38. A method for treating a patient having a disease involving decreased cAMP levels comprising administering to said patient an effective amount of a compound according to claim 1.

39. A method of inhibiting PDE4 enzyme activity in a patient comprising administering to said patient an effective amount of a compound according to claim 1.

40. A pharmaceutical composition comprising a compound according to claim 1 and a pharmaceutically acceptable carrier.

41. A composition according to said composition contains 0.1–50 mg of said compound.

42. A method of treating a patient suffering from memory impairment due to a neurodegenerative disease comprising administering to said patient an effective amount of a compound according to claim 1.

43. A method of treating a patient suffering from memory impairment due to an acute neurodegenerative disorder comprising administering to said patient an effective amount of a compound according to claim 1.

44. A method of treating a patient suffering from an allergic or inflammatory disease comprising administering to said patient an effective amount of a compound according to claim 1.

45. A compound of the formula

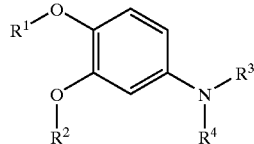

wherein:
R¹ is H, tert-butydimethylsilyl, ³H₃C—, ¹⁴CH₃—, ¹¹CH₃— or a phenolic protective group;
is cycloalkyl having 3 to 10 carbon atoms, which is unsubstituted or substituted one or more times by halogen, hydroxy, oxo, cyano, alkyl having 1 to 4 carbon atoms, alkoxy having 1 to 4 carbon atoms, or combinations thereof;
R³ is a heteroarylalkyl group, wherein the heteroaryl portion is furyl, thienyl, pyrrolyl, pyrazolyl, imidazolyl, triazolyl, terrazolyl, dithialyl, oxathialyl, isoxazolyl, oxazolyl, thiazolyl, isothiazolyl, oxadiazolyl, oxatriazolyl, dioxazolyl, oxathiazolyl, thiadiazolyl, pyridyl, pyridazinyl, pyrimidinyl, pyrazinyl, triazinyl, oxazinyl, isoxazinyl, oxathiazinyl, oxathiazinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, beuzopyranyl, quinolinyl, isoquinolinyl, cinnolinyl, quinazolinyl, naphthyridinyl, or benzoxazinyl, and wherein the alkyl portion, which is branched or unbranched, has 1 to 5 carbon atoms, the heteroarylalkyl group is unsubstituted or substituted one or mare times in the heteroaryl portion by halogen, alkyl, alkoxy, cyano, trifluoromethyl, $CF_3O$, nitro, oxo, amino, alkylamino, dialkylamino, or combinations thereof and/or substituted in the alkyl portion by halogen, cyano, or methyl or combinations thereof;

$R^4$ is aryl having 6 to 14 carbon Moms and which is unsubstituted or substituted one or more times by halogen, alkyl, alkenyl, alkynyl, hydroxy, alkoxy, alkoxyalkoxy, nitro, methylenedioxy, ethylenedioxy, trifluoromethyl, $OCF_3$, amino, aminoalkyl, aminoalkoxy dialkylamino, hydroxyalkyl, hydroxamic acid, hydroxyalkoxy, carboxy, alkoxycarbonyl, cyano, acyl, alkylthio, alkylsulfinyl, alkylsulfonyl, phenoxy, trialkylsilyloxy, $R^5$-L-, or combinations thereof;

$R^5$ is H,
 alkyl having 1 to 8 carbon atoms, which is unsubstituted or substituted one or more times with halogen, $C_{1-4}$-alkyl, $C_{1-4}$-alkoxy, oxo, or combinations thereof,
 alkylamino or dialkylamino wherein each alkyl portion has independently 1 to 8 carbon atoms,
 a partially unsaturated carbocycle-alkyl group wherein the carbocyclic portion has 5 to 14 carbon atoms and the alkyl portion has 1 to 5 carbon atoms, which is unsubstituted or substituted, preferably in the carbocyclic portion, our or more times by halogen, alkyl, alkoxy, nitro, cyano, oxo, or combinations thereof;
 cycloalkyl having 3 to 10 carbon atoms, which is unsubstituted or substituted one or more times by halogen, hydroxy, oxo, cyano, alkoxy, alkyl having 1 to 4 carbon atoms, or combinations thereof,
 cycloalkylalkyl having 4 to 16 carbon atoms, which is unsubstituted or substituted in the cycloalkyl portion and/or the alkyl portion one or more times by halogen, oxo, cyano, hydroxy, alkyl, alkoxy or combinations thereof,
 aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, or combinations thereof, or
 arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or more times by halogen, trifluoromethyl, $CF_3O$, nitro, amino, alkyl, alkoxy, ammo, alkylamino, dialkylamino and/or substituted in the alkyl portion by halogen, cyano, or methyl;

L is a single bond or a divalent aliphatic radical having 1 to 8 carbon atoms wherein one or more —$CH_2$— groups are each optionally replaced by —O—, —S—, —$NR^6$-, —$SO_2NH$—, —$NHSO_2$—, —CO—, —$NR^6CO$—, —$CONR^6$—, —NHCONH—, —OCONH—, —NHCOO—, —SCONH—, —SCSNH—, or —NHCSNH—; and $R^6$ is H, or
 alkyl having 1 to 8 carbon atoms, which is branched or unbranched and which is unsubstituted or substituted one or more times with halogen, $C_{1-4}$-alkyl, $C_{1-4}$-alkoxy, oxo, or combinations thereof; or
a pharmaceutically acceptable salt thereof.

46. A compound selected from:
 3'-(2-Bromoethoxy)-3-cyclopentyloxy-4-methoxy-N-(3 pyridylmethyl)diphenylamine; 4'-[1-(3-Bromopropyl) oxy]-3-cyclopentyloxy-4-methoxy-N-(3-pyridylmethyl)diphenylamine; and 4-hydroxy-3-cyclopentyloxy-N-(3-pyridylmethyl)diphenylamine.

47. A compound according to claim 1, wherein said compound is 3-cyclopentyloxy-4-methoxy-N-(3-pyridylmethyl)diphenylamine or a pharmaceutically acceptable salt thereof.

48. A compound according to claim 1, wherein said compound is N-(3-cyclopentyloxy-4-methoxyphenyl)-N-(3-pyridylmethyl)-3-aminobenzoic acid or a pharmaceutically acceptable salt thereof.

49. A compound according to claim 1, wherein said compound is 3-cyclopentyloxy-3'-ethanesulfonylamino-4-methoxy-N-(3-pyridylmethyl)diphenylamine or a pharmaceutically acceptable salt thereof.

50. A compound according to claim 1, wherein said compound is 3-cyclopentyloxy-4-methoxy-N-(3-pyridylmethyl)diphenylamine.

51. A compound according to claim 1, wherein said compound is N-(3-cyclopentyloxy-4-methoxyphenyl)-N-(3-pyridylmethyl)-3-aminobenzoic acid.

52. A compound according to claim 1, wherein said compound is 3-cyclopentyloxy-3'-ethanesulfonylamino-4-methoxy-N-(3-pyridylmethyl)diphenylamine.

53. A method according to claim 32, wherein said compound is 3-cyclopentyloxy-4-methoxy-N-(3-pyridylmethyl)diphenylamine or a pharmaceutically acceptable salt thereof.

54. A method according to claim 32, wherein said compound is N-(3-cyclopentyloxy-4-methoxyphenyl)-N-(3-pyridylmethyl)-3-aminobenzoic acid or a pharmaceutically acceptable salt thereof.

55. A method according to claim 32, wherein said compound is 3-cyclopentyloxy-3'-ethanesulfonylamino-4-methoxy-N-(3-pyridylmethyl)diphenylamine or a pharmaceutically acceptable salt thereof.

56. A method according to claim 32, wherein said compound is 3-cyclopentyloxy-4-methoxy-N-(3-pyridylmethyl)diphenylamine.

57. A method according to claim 32, wherein said compound is N-(3-cyclopentyloxy-4-methoxyphenyl)-N-(3-pyridylmethyl)-3-aminobenzoic acid.

58. A method according to claim 32, wherein said compound is 3-cyclopentyloxy-3'-ethanesulfonylamino-4-methoxy-N-(3-pyridylmethyl)diphenylamine.

59. A method according to claim 35, wherein said compound is 3-cyclopentyloxy-4-methoxy-N-(3-pyridylmethyl)diphenylamine or a pharmaceutically acceptable salt thereof.

60. A method according to claim 35, wherein said compound is N-(3-cyclopentyloxy-4-methoxyphenyl)-N-(3-pyridylmethyl-3-aminobenzoic acid or a pharmaceutically acceptable salt thereof.

61. A method according to claim 35, wherein said compound is 3-cyclopentyloxy-3'-ethanesulfonylamino-4-methoxy-N-(3-pyridylmethyl)diphenylamine or a pharmaceutically acceptable salt thereof.

62. A method according to claim 38, wherein said compound is 3-cyclopentyloxy-4-methoxy-N-(3-pyridylmethyl) diphenylamine or a pharmaceutically acceptable salt thereof.

63. A method according to claim 38, wherein said compound is N-(3-cyclopentyloxy-4-methoxyphenyl-N-(3-pyridylmethyl)-3-aminobenzoic acid or a pharmaceutically acceptable salt thereof.

64. A method according to claim 38, wherein said compound is 3-cyclopentyloxy-3'-ethanesulfonylamino-4-methoxy-N-(3-pyridylmethyl)diphenylamine or a pharmaceutically acceptable salt thereof.

65. A composition according to claim 40, wherein said compound is 3-cyclopentyloxy-4-methoxy-N-(3-pyridylmethyl)diphenylamine or a pharmaceutically acceptable salt thereof.

66. A composition according to claim 40, wherein said compound is N-(3-cyclopentyloxy-4-methoxyphenyl)-N-(3-pyridylmethyl)-3-aminobenzoic acid or a pharmaceutically acceptable salt thereof.

67. A composition according to claim 40, wherein said compound is 3-cyclopentyloxy-3'-ethanesulfonylamino-4-methoxy-N-(3-pyridylmethyl)diphenylamine or a pharmaceutically acceptable salt thereof.

68. A compound according to claim 1, wherein $R^5$ is H, alkyl having 1 to 8 carbon atoms, which is unsubstituted or substituted one or more times with halogen, $C_{1-4}$-alkyl, $C_{1-4}$-alkoxy, oxo, or combinations thereof, alkylamino or dialkylamino wherein each alkyl portion has independently 1 to 8 carbon atoms, a partially unsaturated carbocycle-alkyl group wherein the portion has 5 to 14 carbon atoms and the alkyl portion has 1 to 5 carbon atoms, which is unsubstituted or substituted, preferably in the carbocyclic portion, one or more times by halogen, alkyl, alkoxy, nitro, cyano, oxo, or combinations thereof, cycloalkyl having 3 to 10 carbon atoms, which is unsubstituted or substituted one or more times by halogen, hydroxy, oxo, cyano, alkoxy, alkyl having 1 to 4 carbon atoms, or combinations thereof, cycloalkylalkyl having 4 to 16 carbon atoms, which is unsubstituted or substituted in the cycloalkyl portion and/or the alkyl portion one or mote times by halogen, oxo, cyano, hydroxy, alkyl, alkoxy or combinations thereof, aryl having 6 to 14 carbon atoms and which is unsubstituted or substituted one or more times by halogen, alkyl, hydroxy, alkoxy, alkoxyalkoxy, nitro, methylenedioxy, ethylenedioxy, trifluoromethyl, amino, aminomethyl, aminoalkyl, aminoalkoxy dialkylamino, hydroxyalkyl, hydroxamic acid, tetrazole-5-yl, hydroxyalkoxy, carboxy, alkoxycarbonyl, cyano, acyl, alkylthio, alkylsulfinyl, alkylsulfonyl, or combinations thereof, or arylalkyl having 7 to 19 carbon atoms, wherein the aryl portion has 6 to 14 carbon atoms and the alkyl portion, which is branched or unbranched, has 1 to 5 carbon atoms, arylalkyl radical is unsubstituted or substituted, in the aryl portion, one or mare times by halogen, trifluoromethyl, $CF_3O$, nitro, amino, alkyl, alkoxy, amino, alkylamino, dialkylamino and/or substituted in the alkyl portion by halogen, cyano, or methyl.

69. A compound according to claim 1, wherein $R^3$ is pyridylmethyl, pyridylpropyl, methylpyridylmethyl, chloropyridylmethyl, dichloropridylmethyl, thienylmethyl, thiazolylmethyl, quinolinylmethyl, isoquinolinylmethyl, furanylmethyl, imidazolylmethyl, methylimidazolylmethyl, or pyrrolylmethyl.

70. A compound according to claim 1, wherein $R^3$ is pyridylmethyl, furanylmethyl, thienylmethyl, pyrrolylmethyl, pyrimidinylmethyl, thiazolylmethyl, isoquinolinylmethyl or quinolinylmethyl, which in each case is substituted or unsubstituted.

71. A compound according to claim 1, wherein $R^4$ is phenyl, naphthyl, or biphenyl, which in each case is unsubstituted or is substituted.

72. A compound according to claim 1, wherein $R^4$ is phenyl, methylphenyl, chlorophenyl, fluorophenyl, vinylphenyl, cyanophenyl, methylenedioxophenyl, ethylphenyl, dichiorophenyl, carboxyphenyl, ethoxycarbonylphenyl, dimethylphenyl, hydroxymethylphenyl, nitrophenyl, or aminophenyl.

73. A compound according to claim 1, wherein $R^1$ is methyl;

$R^2$ is cyclopentyl;

$R^3$ is pyzidylmethyl, thienylmethyl, pyridylpropyl, pyrazinylmethyl, which in each case is substituted or unsubstituted, or methyl, ethyl, or propyl; and $R^4$ is phenyl, naphthyl, or biphenyl, which in each case substituted or unsubstituted.

74. A compound according to claim 1, wherein wherein $R^3$ is thienylmethyl, pyridylmethyl, quinolinylmethyl, pyrazinylmethyl, furylmethyl, or thiazolylmethyl, which in each case is substituted or unsubstituted, and $R^4$ is phenyl which is substituted or unsubstituted.

75. A compound according to claim 1, wherein $R^3$ is 3-thienylmethyl, 4-pyridylmethyl, 2,6-dichloro-4-pyridylmethyl, 2-quinolinylmethyl, 3-quinolinylmethyl, 4-quinolinylmethyl, 2-pyrazinylmethyl, 3-furylmethyl, 2.6-dichloro-4-pyridylmethyl, 2-thienylmethyl, 3-pyridylmethyl, 2-chloro-5-pyridylmethyl, 2-thiazolylmethyl, 4-chloro-3-pyridylmethyl, 4-methyl-3-pyridylmethyl, 2-thiazolylmethyl, 2-chloro-3-pyridylmethyl, or 6-chloro-3-pyridylmethyl, and $R^4$ is phenyl.

* * * * *